(12) United States Patent
Hirai et al.

(10) Patent No.: US 8,941,835 B2
(45) Date of Patent: Jan. 27, 2015

(54) FOREIGN SUBSTANCE DETECTION DEVICE, MOVING BODY CONTROL SYSTEM INCLUDING FOREIGN SUBSTANCE DETECTION DEVICE, AND MOVING BODY INCLUDING MOVING BODY CONTROL SYSTEM

(71) Applicants: Hideaki Hirai, Kanagawa (JP); Izumi Itoh, Tokyo (JP)

(72) Inventors: Hideaki Hirai, Kanagawa (JP); Izumi Itoh, Tokyo (JP)

(73) Assignee: Ricoh Company, Ltd., Tokyo (JP)

( * ) Notice: Subject to any disclaimer, the term of this patent is extended or adjusted under 35 U.S.C. 154(b) by 0 days.

(21) Appl. No.: 13/945,029

(22) Filed: Jul. 18, 2013

(65) Prior Publication Data
US 2014/0029008 A1 Jan. 30, 2014

(30) Foreign Application Priority Data

Jul. 30, 2012 (JP) .................................. 2012-168638
May 14, 2013 (JP) .................................. 2013-101863

(51) Int. Cl.
*G01N 21/55* (2014.01)
*G01N 21/552* (2014.01)
*B60S 1/08* (2006.01)
*G06K 9/00* (2006.01)

(52) U.S. Cl.
CPC ............. *G01N 21/552* (2013.01); *B60S 1/0844* (2013.01); *G06K 9/00791* (2013.02)

USPC .......................................................... 356/445

(58) Field of Classification Search
USPC .......................................................... 356/445
See application file for complete search history.

(56) References Cited

U.S. PATENT DOCUMENTS 7,002,480 B2 * 2/2006 Kobayashi et al. ........... 340/602

FOREIGN PATENT DOCUMENTS

JP 2010-014494 1/2010

* cited by examiner

*Primary Examiner* — Roy M Punnoose
(74) *Attorney, Agent, or Firm* — Harness, Dickey & Pierce, P.L.C.

(57) ABSTRACT

A foreign substance detection system includes an optical device having an input surface through which is part of light emitted from a light source enters the optical device and a transparent face, provided in close contact with an inner surface of a glass, to transmit a light reflected from an area where a substance is not present on an outer surface of the glass toward a first light-receiving member; a light-guiding member to guide another part of the light that does not pass through the input surface, the guided light being to be reflected from an area where a substance is present on an inner surface of the glass toward a second light-receiving member; and an foreign substance detection processor to detect an outer substance based on the first light-receiving member and detect the inner substance based on the second light-receiving member.

10 Claims, 19 Drawing Sheets

PROCESS TO DETECT PARAMETER OF VEHICLE DETECTING IMAGE REGION

FIG. 31A

| DETERMINATION RESULT | DAYTIME | | | | | | | |
|---|---|---|---|---|---|---|---|---|
| | SHINE | DRIZZLE | RAIN | HEAVY RAIN | SPLASH | FOGGY | ICY |
| EXPOSURE TIME FOR REGION 231 < THRESHOLD VALUE A | NO | NO | NO | NO | NO | NO | NO |
| LUMINANCE DIFFERENCE IN REGION 231 < THRESHOLD VALUE B | YES | YES | YES | NO | NO | NO | NO |
| CAN HORIZONTAL EDGE OF HOOD EDGE IN REGION 231 BE DETECTED ? | YES | YES | YES | NO | NO | NO | NO |
| LUMINANCE AVERAGE IN REGION 232A < THRESHOLD VALUE C | NO | YES | YES | YES | YES | YES | YES |
| LUMINANCE AVERAGE IN REGION 232B < THRESHOLD VALUE C' | — | — | — | — | — | YES | — |
| LUMINANCE DISPERSION VALUE IN REGION 232A > THRESHOLD VALUE D | NO | NO | YES | YES | YES | NO | NO |
| CHANGE IN LUMINANCE AVERAGE IN REGION 232A < THRESHOLD VALUE E | YES | YES | YES | YES | NO | YES | YES |
| OCCUPANCY OF FOREIGN SUBSTANCES IN REGION 232A < THRESHOLD VALUE F | YES | YES | YES | YES | YES | NO | NO |
| AMBIENT TEMPERATURE > THRESHOLD VALUE G | YES | YES | YES | YES | YES | YES | NO |

FIG. 31B

| DETERMINATION RESULT | NIGHTTIME | | | | | | | |
|---|---|---|---|---|---|---|---|---|
| | SHINE | DRIZZLE | RAIN | HEAVY RAIN | SPLASH | FOGGY | ICY |
| EXPOSURE TIME FOR REGION 231 < THRESHOLD VALUE A | YES | YES | YES | YES | YES | YES | YES |
| LUMINANCE DIFFERENCE IN REGION 231 < THRESHOLD VALUE B | NOT IN USE | NOT IN USE | NOT IN USE | NOT IN USE | NOT IN USE | NOT IN USE | NOT IN USE |
| CAN HORIZONTAL EDGE OF HOOD EDGE IN REGION 231 BE DETECTED ? | NOT IN USE | NOT IN USE | NOT IN USE | NOT IN USE | NOT IN USE | NOT IN USE | NOT IN USE |
| LUMINANCE AVERAGE IN REGION 232A < THRESHOLD VALUE C | NO | YES | YES | YES | YES | YES | YES |
| LUMINANCE AVERAGE IN REGION 232B < THRESHOLD VALUE C' | — | — | — | — | — | YES | — |
| LUMINANCE DISPERSION VALUE IN REGION 232A > THRESHOLD VALUE D | NO | NO | YES | YES | YES | NO | NO |
| CHANGE IN LUMINANCE AVERAGE IN REGION 232A < THRESHOLD VALUE E | YES | YES | YES | YES | NO | YES | YES |
| OCCUPANCY OF FOREIGN SUBSTANCES IN REGION 232A < THRESHOLD VALUE F | YES | YES | YES | YES | YES | NO | NO |
| AMBIENT TEMPERATURE > THRESHOLD VALUE G | YES | YES | YES | YES | YES | YES | NO |

FIG. 32

| CONDITION | WIPER CONTROL | DEFROSTER CONTROL |
|---|---|---|
| SHINE | DO NOT OPERATE | DO NOT OPERATE |
| DRIZZLE | OPERATE AT A SLOW SPEED | DO NOT OPERATE |
| RAIN | OPERATE AT A MEDIUM SPEED | DO NOT OPERATE |
| HEAVY RAIN | OPERATE AT A FAST SPEED | DO NOT OPERATE |
| SPLASH | OPERATE AT A FAST SPEED | DO NOT OPERATE |
| FOGGY | OPERATE AT A SLOW SPEED | OPERATE |
| ICY | DO NOT OPERATE | OPERATE |

…

FOREIGN SUBSTANCE DETECTION DEVICE, MOVING BODY CONTROL SYSTEM INCLUDING FOREIGN SUBSTANCE DETECTION DEVICE, AND MOVING BODY INCLUDING MOVING BODY CONTROL SYSTEM

CROSS-REFERENCE TO RELATED APPLICATIONS

This patent application is based on and claims priority pursuant to 35 U.S.C. §119 to Japanese Patent Application No. 2012-168638, filed on Jul. 30, 2012 and No. 2011-101863 filed on May 14, 2013 in the Japan Patent Office, the entire disclosure of which are hereby incorporated by references herein.

BACKGROUND

1. Technical Field

The present disclosure relates to a foreign substance detection device to detect a substance on a light-transmissive member used for vehicle, ship, and plane, and buildings, etc., a moving body control system to control a control target device in a moving body, and a moving body including the moving body control system.

2. Related Art

JP-2010-014494-A discloses a foreign substance detection device (foreign substance detection device) to detect foreign substance present on a windshield of a vehicle. In the foreign substance detection device, a camera captures an image showing the foreign substance of raindrops present on an outer surface of the windshield with light emitted from a light-emitting member positioned on an inner surface side of the windshield. The camera receives the light emitted from the tight emitting member and totally reflected from a non-substance detected area where the raindrop is not present, and the camera does not receive the light reflected a substance detected area where the raindrop is present because the light is transmitted through the outer surface of the windshield. Accordingly, the area whose luminance is low is determined as the area where the raindrop is present.

SUMMARY

Herein, the conventional foreign substance detection device detects only the substance present on one surface of the planner light-transmissive member of the windshield. In the above-described foreign substance detection device using the totally reflection condition, the substance present on both surfaces of the planner member cannot be detected. However, the market demands to detect the substance present an not only one surface of the planner member but also the other surface thereof. For example, it is desired to detect the substance (e.g., fog of minuscule droplet of water) present on an inner surface of the windshield, in addition to the substrates such as raindrop present on the outer surface of the windshield.

In view of the above, it is a general object of the present invention to provide a foreign substance detection system, a moving body controller, and a moving body, each of which is capable of detecting subjected present on a planner member positioned near the foreign substance detection system with improved accuracy.

In order to achieve the above-mentioned object, according to one aspect of the present disclosure, there is provided the foreign substance detection system, provided close to a planner light-transmissive plane member, detects substances present on the planner light-transmissive plane member. The foreign substance detection system includes a light emitting member, an optical device, a light-guiding member, a first light receiving member, a second light receiving member, and a foreign substance detection processor. The light emitting member emits light to the inner surface of the planner light-transmissive member. The optical device has an input surface and a transparent face. A part of the light emitted from the light emitting element enters the optical device through the input surface. The transparent face, provided in close contact with the inner surface of the planner light-transmissive member, transmits as light reflected from an outer non-substance detected area where a substance is not present on an outer surface of the planner light-transmissive member. The light-guiding member guides another part of the light that does not pass through the input surface of the optical device toward the planner light-transmissive member. The guided light is to be reflected from an inner substance detected area where a substance is present on the inner surface of the planner light-transmissive member. The first light receiving member receives the light reflected from the outer non-substance detected area where the substance is not present on the outer surface of the planner light-transmissive member and transmitted through the transparent face of the optical device. The second light receiving member receives the light guided by the light-guiding member and reflected from the inner substance detected area where the substance is present on to the inner surface of the planner light-transmissive member. The foreign substance detection processor detects the substance present on the outer surface of the light-transmissive plane member based on the receiving result of the first light receiving member, and detects the substance present on the inner surface of the planner light-transmissive member based on the receiving result of the second light receiving member.

In another aspect of the present disclosure, there is provided a moving body controller, installed in a moving body that has at least one operational device, includes at least one control device and a foreign substance detection system. The control device controls operation of the operational device or movement of the moving body. The foreign substance detection system positioned close to a window, detects substances present on the window, operatively connected to the control device. The foreign substance detection system includes a light emitting member, an optical device, a light-guiding member, a first light receiving member, a second light receiving member, and a foreign substance detection processor. The light emitting element emits light to the inner surface of the window. The optical device has an input surface and a transparent face. A part of the light emitted from the light emitting element enters the optical device through the input surface. The transparent face, provided in close contact with the inner surface of the planner light-transmissive member, transmits a light reflected from an outer non-substance detected area where a substance is not present on an outer surface of the window. The light-guiding member guides another part of the light that does not pass through the input surface, and the guided light is to be reflected from an inner substance detected area where a substance is present on an inner surface of the planner member. The first light receiving member receives the light reflected from the outer non-substance detected area where the substance is not present on the outer surface of the window and transmitted through the transparent face of the optical device. The second light receiving member receives the light guided by the light-guiding member and reflected from the inner substance detected area where the substance is present on to the inner surface of the window. The foreign substance detection processor detects the substance present on the outer surface of the window based on the receiving result of the first light receiving member, detects the substance present on the inner surface of the window based on the receiving result of the second light receiving member, and outputs the detection result to the control devices.

Yet another aspect of the present disclosure, a moving body includes a window, target devices and the above-described moving body controller, to control the target devices in the moving body.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein;

FIGS. 31A and 31B are tables illustrating determination criteria of windshield condition determination process; and FIG. 32 is a table illustrating the command process depending on the windshield condition determination result.

DETAILED DESCRIPTION

Figure 1:
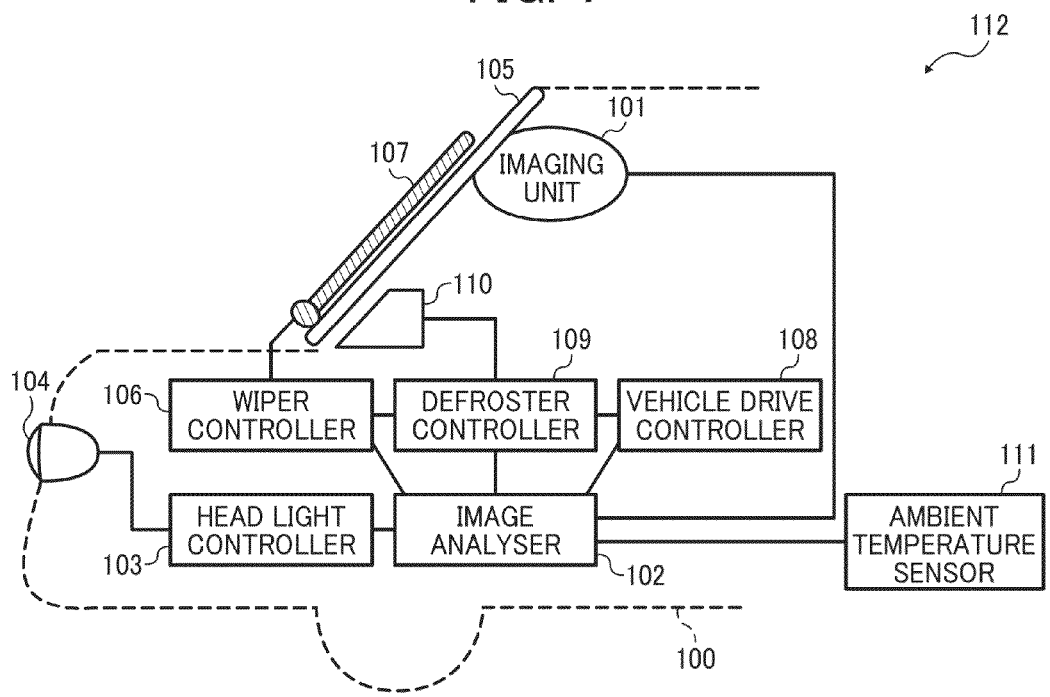
FIG. 1 is a schematic diagram illustrating an in-vehicle mount control system.

In describing preferred embodiments illustrated in the drawings, specific terminology is employed for the sake of clarity. However, the disclosure of this patent specification is not intended to be limited to the specific terminology so selected, and it is to be understood that each specific element includes all technical equivalents that have the same function, operate in a similar manner, and achieve a similar result.

Referring now to the drawings, wherein like reference numerals designate identical or corresponding parts throughout the several views thereof, and particularly to FIGS. 1 through 32, a foreign substance detection device according to illustrative embodiments of the present disclosure is described.

A description is given of a control system to control vehicle-installed devices according to an example embodiment, in which an image capturing device is installed in a vehicle. The image capturing device can be used with the control system to control vehicle-installed devices, but the image capturing device can be applied for other systems having an object detector or object detection apparatus to conduct the detection of objects based on captured images, which may be captured by the image capturing device. The vehicle may not be limited to any specific vehicles but may include various types of vehicles such as automobiles, ship, robots, or the like.

FIG. 1 shows a schematic configuration of an in-vehicle mount control system 112 according to the present disclosure. A vehicle 100 such as automobiles may include the in-vehicle mount control system 112 to control vehicle-installed devices, and an image capturing unit 101. Such vehicle 100 may be referred to as a detector-equipped vehicle in this disclosure. In this disclosure, for the simplicity of explanation, the vehicle 100 installs the detector to detect other objects on road or the like. It should be noted that other vehicles can be also installed with the detector. The detector can be used for any type of vehicles, or moving objects used under various environmental conditions. The image capturing device can capture views of an object ahead of the vehicle 100 as captured image data. Based on the captured image data, the control system 112 to control vehicle-installed devices performs light control of headlight, wiper-drive control defroster control, control of other vehicle-installed devices, or the like.

An image capturing device 200 used for the control system 112 to control vehicle-installed devices is disposed in an image capturing unit 101. The image capturing device captures views of an area ahead of the vehicle 100 (vehicle-front-area of the vehicle 100), wherein vehicle-front-area may be referred to as image capturing area or captured image area. For example, the image capturing, device 200 captures a vehicle-front-area of the vehicle 100 when the vehicle 100 is running. The image capturing device 200 may be, for example, disposed near a rear-view mirror and a windshield 105 of the vehicle 100. Image data captured by the image capturing device 200 of the image capturing unit 101 is input to the image analyzer 102. The image analyzer 102 analyzes the captured image data, transmitted from the image capturing device, in which the image analyzer 102 can be used to compute information regarding other vehicles existing in a front direction of the vehicle 100, such as vehicle position, direction of the other s such as a point of the compass (e.g., north, south, east, west), and distance of the other vehicles with respect to the vehicle 100.

An ambient sensor 111 to detect an ambient temperature is provided on the vehicle 100. The image analyzer 102 uses the detection result of the ambient sensor 111 as needed to detect various conditions. In the present embodiment, the detection result of the ambient sensor 111 is used to determine whether the windshield 105 is iced or not. Further, the image analyzer 102 can be used to detect a substance such as raindrops, foreign particles, or the like, which may be present on the windshield 105. Further, the image analyzer 102 can be used for detecting a detection-target object existing on road surfaces such as a lane (e.g., white line) or the like from the image capturing area. Further, the image analyzer 102 can be used for detecting other vehicles. Specifically, by recognizing a tail lamp of the other vehicle, the image analyzer 102 can detect a front-running vehicle (or vehicle ahead) running in front of the vehicle 100 in the same running direction. In another example, by recognizing a headlight of the other vehicle, the image analyzer 102 can detect an oncoming vehicle coming toward the vehicle 100 such as head-to-head direction. As such, the image analyzer 102 can be used as a substance detection processor, and an object detection processor.

The detection result such as the computation result of the image analyzer 102 can be transmitted to the headlight controller 103. For example, the headlight controller 103 generates a headlight control signal to control a headlight 104 based on distance data computed by the image analyzer 102, wherein the headlight 104 is one of devices installed in the vehicle 100. Specifically, for example, a switching control of high beam/low beam of the headlight 104 is conducted, and a light-dimming control is partially conducted for the headlight 104 to prevent projection of high intensity light of the headlight of the vehicle 100 to eyes of drivers of front-running vehicles and oncoming vehicles, by which the drivers of other vehicles are not dazzled by light coming from the headlight of the vehicle 100, thus providing a sufficient field of view for the driver of the vehicle 100.

The computation result of the image analyzer 102 is also transmitted to the wiper controller 106. The wiper controller 106 controls a wiper 107 to remove a substance on the windshield 105 such as raindrops, foreign panicles, or the like from the windshield 105 of the vehicle 100. The wiper controller 106 generates a wiper control signal to control the wiper 107 upon receiving the detection result of foreign particles from the image analyzer 102. When the wiper control signal generated by the wiper controller 106 is transmitted to the wiper 107, the wiper 107 is activated to provide the field of view for the driver of the vehicle 100.

Further, the computation result of the image analyzer 102 is also transmitted to a vehicle controller 108, which controls the driving of the vehicle 100. If the vehicle 100 deviates or departs from the vehicle lane, defined by the lane (e.g., white line), based on the detection result of the lane detected by the image analyzer 102, the vehicle controller 108 activates an alarm or warning to the driver of the vehicle 100, and activates a cruise control system 112 so as to control a steering wheel and/or brake of the vehicle 100.

In addition, the vehicle controller 108 compares road sign information with the vehicle driving state based on the detection result of the load sign detected by the image analyzer 102. For example, if the vehicle controller 108 determines that the driving speed (vehicle driving state) becomes close to the limited speed (road sign information), the vehicle controller 108 alerts the driver of the vehicle 100. If the vehicle controller 108 determines that the driving speed exceeds the limited speed, the vehicle controller 108 activates a cruise control system to control the brake of the vehicle 100.

In addition, the calculation result of the image analyzer 102 is transmitted to the defroster control unit 109. The defroster control unit 109 generates a defroster control signal that controls the defroster 110 based on the detection result of icing and fogging of the windshield 105. When the defroster control signal generated by the defroster controller 109 are transmitted to the defroster 110, the defroster 110 is activated to drive a fan to send winds or provide heat to the windshield 105 to remove the icing and fogging of the windshield 105. The control of the defroster 105 is further described below.

Figure 2:
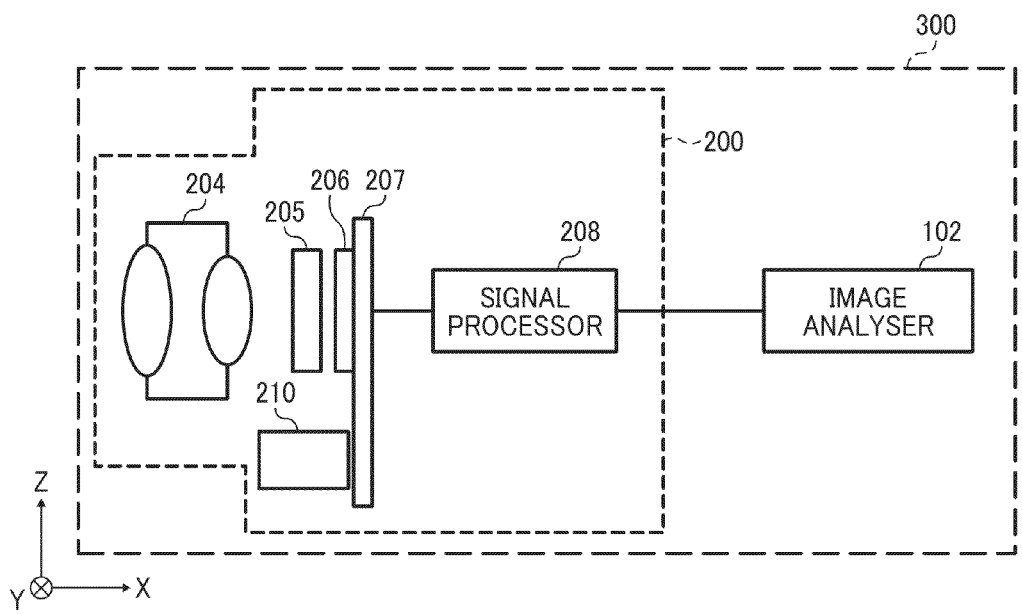
FIG. 2 is a schematic diagram illustrating a foreign substance detection system, including an image capturing unit, in the in-vehicle mount control system shown in FIG. 1.

FIG. 2 shows a schematic configuration of a foreign substance detection system 300, including the image capture device 200 that is installed in the image capturing unit 101. The image capture device 200 mainly includes an imaging lens 204, the optical filter 205, a sensor board (substrate) 207, and a signal processor 208. The sensor board 207 is provided with the image sensor 206 composed of a two-dimensional pixel array, which can be configured by arraying a number of light receiving elements in two dimensional directions. Each of light receiving elements of the image sensor 206 receives light having a light level, and the sensor board 207 outputs analog electrical signals corresponding to the received light levels to the signal processor 208. Upon receiving the analog, electrical signals, the signal processor 208 converts the analog electrical signals to digital electrical signals to generate and output the captured image data. In the present embodiment, the light source 210 is mounted on the sensor board 207. The light source 210 is provided for detecting the substances present on the outer surface (other face) of the windshield 105. The following describes the example when the detection substances are the raindrops.

In the present embodiment, the image capturing unit 101 is provided so that the optical axis of the imaging lens 204 is in line with the horizontal direction. The configuration is not limited above. For example, the imaging lens 204 can be provided so as to direct a specified direction with reference to the horizontal direction (X direction shown in FIG. 2). The imaging lens may be constituted by multiple lenses, with the focus point being set far from the position of the windshield 105. The focus point of the imaging lens 204 may be set at the position at infinity or the position between the position at infinity and the windshield 105.

The optical filter 205, provided in a subsequent stage of the imaging lens 204, has a function to limit the wavelength range of the light emitted to the imaging sensor 206. In the present embodiment, the optical filter 205 is provided for suppressing the influence from the ambient light outside of the vehicle 100 when the condition of the windshield 105 is detected based on the reflection light from the light source 210. Accordingly, in a configuration in which the detection accuracy in detecting the condition of the windshield 105 is sufficient without the optical filter 205, the optical filter 205 may be omitted.

The image sensor 206 is constituted by multiple light-receiving elements to receive the light transmitting the optical filter 205, each of which performs photoelectric conversion. It is to be noted that, while the respective pixels on the image sensor 206 is simplified in the following figures, the image sensors 206 can be formed by several hundred thousand pixels arranged in an array in two-dimensional direction. The image sensor 206 may be constituted by any desired image sensor, such as a charge coupled device (CCD) or complementary metal oxide semiconductor (CMOS).

When the signal processor 208 receives the analog electrical signal (amount of the incident lights input to the light-receiving elements) photoelectrically converted by the image sensor 206 and output from the sensor board 207, the signal processor 208 converts the analog signal to the digital signal to generate captured image data. The signal processor 208 is electrically connected to the image analyzer 102. When the signal processor 208 receives the electrical signals such as analog signals output from the image sensor 206, the signal processor 208 converts the analog signals to digital signals to be used as captured image data, including brightness or intensity data of each pixel on the image sensor 206. The signal processor 208 outputs the captured image data to a later stage unit with horizontal/vertical synchronization signals of image.

The image analyzer 102 controls the capturing operation of the image capturing unit 101 in addition to analyzing the captured image data transmitted from the image capturing unit 101. The image analyzer 102 calculates the suitable exposure amount for respective capturing targets (objected positioned ahead of the vehicle, and raindrop, icing, and fogging present on the windshield 105) of the image sensor 206, based on the captured image data transmitted from the image capturing unit 101, and then sets the suitable exposure amount (exposure time) for respective capturing targets. In addition, the image analyzer 102 operates adjustment of the light-emission timing of the light source 210 in cooperation with adjustment of the exposure amount. The image analyzer 102 detects information of the road surface condition and the road sign based on the captured image data transmitted from the image capturing unit 101 and detects the conditions of the windshield 105 (adhesion of the substance, icing and fogging). In addition, the image analyzer 102 calculates the position, direction and distance of another vehicle positioned in front of the vehicle 100 based on the captured image data transmitted from the image capturing unit 101.

Figure 3:
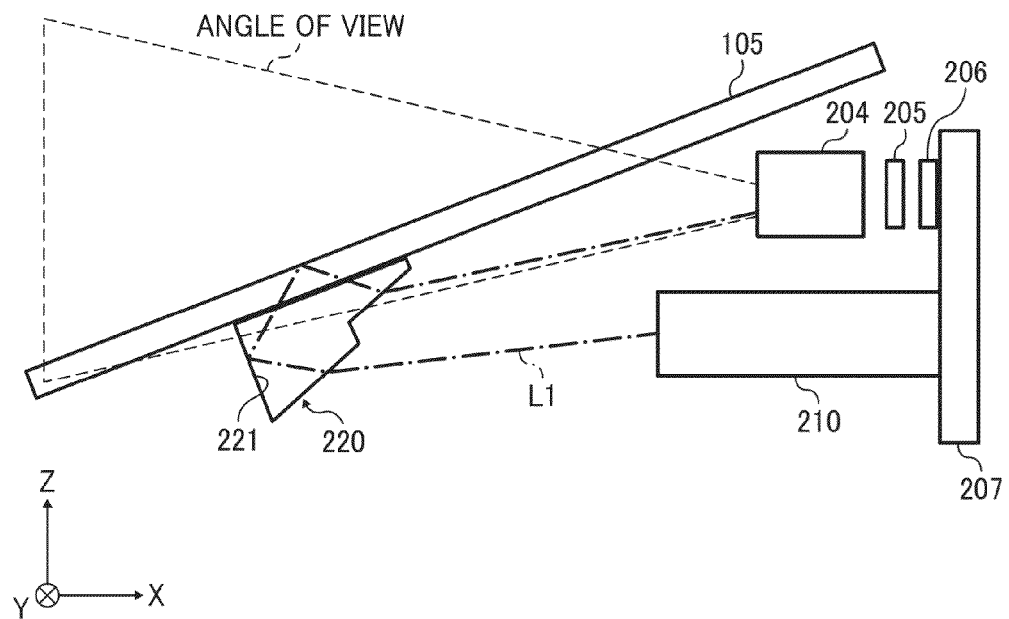
FIG. 3 is a diagram illustrating an optical functional diagram of the image capturing unit in the foreign substance detection system.
Figure 4:
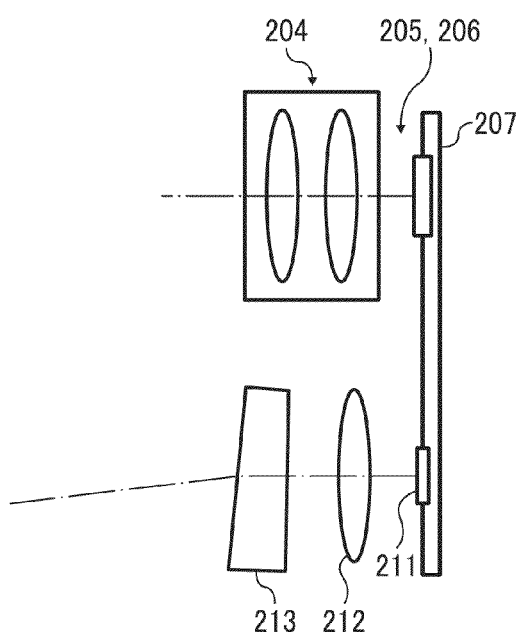
FIG. 4 shows one example of a schematic diagram illustrating a light source disposed in the image capturing unit.
Figure 5:
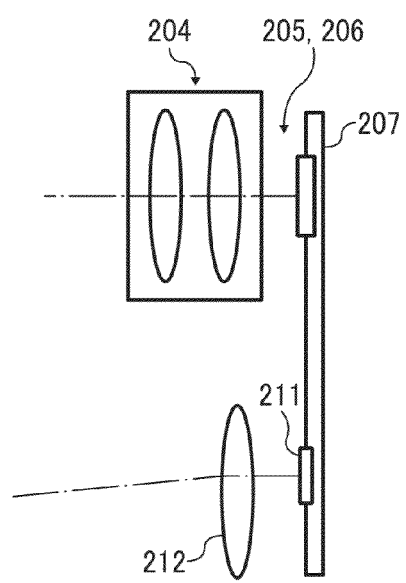
FIG. 5 shows another example of a schematic diagram illustrating a light source in the image capturing unit.

FIG. 3 is a diagram illustrating an optical system of the image capturing unit 101. The light source 210 of the present disclosure emits light to detect the substances (raindrop, ice, and fog) present on the windshield 105. The light source 210 includes multiple light emitting diodes (LED) as luminescent elements. By providing multiple luminescent elements, compared to a single luminescent element, a detecting range in which the substances present on the windshield 105 are detected broaden, and the accuracy in detecting the condition changes of the windshield 105 is improved.

In the present embodiment, since the LEDs are mounted on the image sensor 206 on which the sensor hoard 207 is mounted, the number of substrates can be decreased than the case in which the LED are provided separately. By arranging the multiple LEDs in one or more rows along the Y direction, illumination that allows capturing of the windshield image, which is shown in a lower area of the image area corresponding to the image ahead of the vehicle 100, can be equalized over the image area, which is described detail in below.

The light source 210 is provided on the sensor hoard 207 so that a certain angle is formed between the optical axes of the light emitted from the light source 210 and the optical axis of the imaging lenses 204. The light source 210 is positioned so that the illumination range in which the light source 210 emits light to the windshield 105 is set within an angle of view (view angle) of the imaging lens 204. The light source 210 is constituted by arranging one or more light emitting diode (LED) and/or semiconductor laser diode (LD). In order not to dazzle the driver in the oncoming vehicle and pedestrian, it is preferable to avoid the use of visible light for the light emitting wavelength of light source 210. For example, a wavelength range having a value longer than the visible light and within the wavelength range defined by the light sensitivity of the image sensor 206 (for example, infrared light having wavelength range between 800 nm and 1000 nm) is used as the light emitting wavelength of light source 210. The drive control to control light emitting timing of the light source 210 is performed in cooperation with acquiring of the image signal from the signal processor 208, under control of the image analysis unit 102

As the light is emitted from the light source 210, the condition of the light reflected from the windshield 105 is changed depending on the condition change of the windshield 105, such as raindrop present on the outer surface of the windshield 105, an ice covered area where night dew is iced, and fog on the inner surface of the windshield 105 by moisture. The condition change of the reflection light can be ascertained by analyzing the captured image acquired by the image sensor 206 via the optical filter 205.

By causing, the optical axis of the LED 211 and the sensor surface normal line of the image sensor 206 of the image capturing device 200 be directed to a normal line direction relative to a substrate face, the manufacturing process can be simplified.

However, in the present embodiment, since the light illumination direction of the light source 210 and the capturing direction (optical direction of the image lens 206) are set at different directions, providing the LED 211 of the light source 210 and the image sensor 206 of the image capturing device 200 on the same sensor board 207 would be difficult.

In order to solve this problem, in a configuration in which the LED 211 of the light source 210 and the image sensor 206 of the image capturing device 200 are provided on the same sensor board 207, for example, an optical-path changing member that changes an optical path of the light emitted from the LED 211 may be provided on the light source 210 side. As for the optical-path changing member, for example, a polarization prism 213 like that shown in FIG. 4, an eccentrically disposed collimate lenses 212 like that shown in FIG. 5, and a taper optical-path changing member 215 of FIG. 6 may be used. Herein, when the collimate lens 212 is used, the collimate lenses 212 are provided for the same number of the LEDs 211; in this case, the lens array in which the lenses are lineally arranged in the Y direction may be used.

Figure 6:
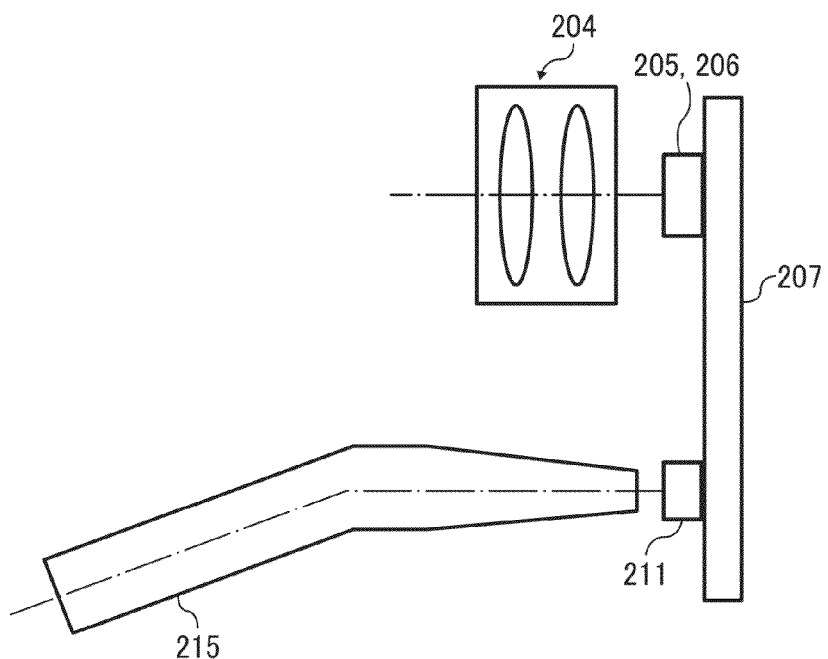
FIG. 6 shows yet another example of a schematic diagram illustrating a light source in the image capturing unit.

In one configuration of the optical-path changing member shown in FIG. 6, the taper optical-path changing member 215 is provided on the output side of the multiple LED 211 mounted on the sensor board 207. With this configuration, the light from the LED 211 is reflected from inner faces of the taper optical-path changing member 215 while passing through the taper optical-path changing member 215, and then the light direction is adjusted to an angle near parallel to the optical axis direction on of the LED 211 to output from the taper optical-path changing member 215.

Accordingly, by providing the taper optical-path changing member 215, dispersion in the light emission angle can be narrower. A light exit area of the taper optical-path changing member 215 is configured so that light emitted from the light source 210 is directed to a desired direction for outputting. In the configuration shown in FIG. 6, the light whose luminance distribution is uniformed within the narrow area can be emitted to the desired direction. Therefore, the condition of the windshield 105 can be accurately detected, and the process load can be alleviated in correction operation such as to correct brightness unevenness.

It is to be noted that, although the light source 210 is mounted on the sensor board 207 on which the image sensor 206 is mounted, alternatively, the light source 210 may be mounted on a substrate different from that on which the image sensor 206 is mounted.

In the example shown in FIG. 3, the image capturing unit 101 includes a reflection-polarization prism 220 functioning as an outer surface substance detecting optical member, having a reflection face (surface) 221 that reflects the light from the light source 210 to guide the light to the windshield 105. In order to guide the light from the light source 210 to the windshield 105 appropriately, the reflection-polarization prism 220 is disposed so that one face 222 (shown in FIG. 12) of the reflection-polarization prism 220 closely contacts the inner surface of the windshield 105. More specifically, the reflection-polarization prism 220 is attached to the inner surface of the windshield 205 to maintain a certain positional relation with respect to the other device such as the light source 210 and the windshield 205. With this structure, even when an emission angle of the light emitted from the light source 210 to the reflection-polarization prism 220 is changed within a certain range, of the light emitted from the light source 210 and secularly reflected from the reflection face 221 of the reflection-polarization prism 220, a specular reflection light specularly reflected from the non-detected area where the raindrop (detection target) is not detected on the outer surface of the windshield 205, is received at the image sensor 206.

When the reflection-polarization prism 220 is attached to the inner surface of the windshield 105, it is desirable to interpose, an infill, such as a gel and a seal member, formed of clear material between the reflection-polarization prism 220 and the inner surface of the windshield 105, thus improving adhesion therebetween. With this configuration, by preventing an air layer and air bubble from intervening a gap between the reflection-polarization prism 220 and the windshield 105, the occurrence of fogging therebetween is prevented.

In addition, it is desirable that a refractive index of the infill has an intermediate index value between refractive index values of the reflection-polarization prism 220 and the windshield 105. With this setting, Fresnel reflection losses between the infill and the reflection-polarization prism 220 and between the infill and the windshield 105 can be set smaller. Herein, Fresnel reflection means the reflection generated between or among multiple materials whose refractive indexes are different each other.

As illustrated in FIG. 3, the reflection-polarization prism 220 specs reflects the light emitted from the light source 210 at the reflection face 221 once for guiding the light to the inner surface of the windshield 105. The reflection face 221 of the reflection-polarization prism 220 is set so that the reflected light is entered to the outer surface of windshield 105 at an incident angle of φ degrees. The incident angle φ is equal to or greater than about 42°, and equal to or less than about 62°, and approximately in a range between 42° and 62°. The suitable incident angle φ is a critical angle at which the light is totally reflected from the outer surface of the windshield 105, defined by the refractive index difference between the air and the outer surface of the windshield 105.

Accordingly, in the present embodiment, in a state in which the substances (e.g., raindrops) is not present on the outer surface of the windshield 105, all of light is reflected from the outer surface of the windshield 105 without penetrating through the outer surface of the windshield 105. Herein, a lower limit of the range of the incident angle φ is determined based on the condition in which the light is totally reflected from an outer non-substance detected area of the outer surface of the windshield 105 to which the substance (raindrop) is not present.

The upper limit of the incident angle φ is determined based on the condition in which the total reflection condition is not satisfied in an outer substance detected area of the outer surface of the windshield 105 to which the substance (raindrop) is present. More specifically, when the substances of raindrop (refractive index=1.38) different from the air (refractive index=1) is present on the outer surface of the windshield 105, the total reflection condition is not met, and the light is penetrated through the outer substance detected area where the raindrop is present on the outer surface of the windshield 105.

With this setting, in the captured image, a high luminance image is acquired by the image sensor 206 that receives the light reflected from the outer non-substance detected area in the outer surface of the windshield 105 to which the raindrop is not present, and a low luminance image is acquired by the image sensor 206 that receives the light reflected from the outer-substance detected area in the outer surface of the windshield 105 wherein the raindrop is present because the amount of reflection light is decreased. Accordingly, contrast between a raindrop detected area and a raindrop non-detected area is generated in the captured image.

Figure 7:
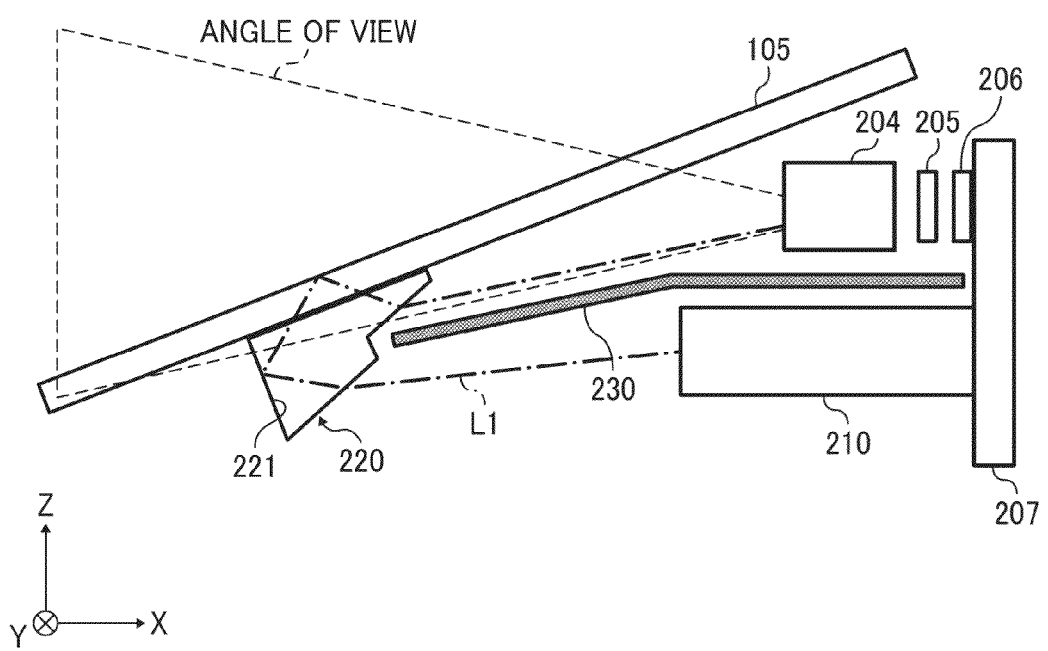
FIG. 7 shows yet another example of a schematic diagram illustrating the image capturing unit includes a shield member disposed between the light source and an imaging lens.

Herein, in order to prevent the diffusion components of the light emitted from the the source 210 from entering be image sensor 206 to deteriorate the image signal, a shield member 230 may be provided between the light source 210 and the imaging lens 204, as illustrated in FIG. 7.

Figure 8:
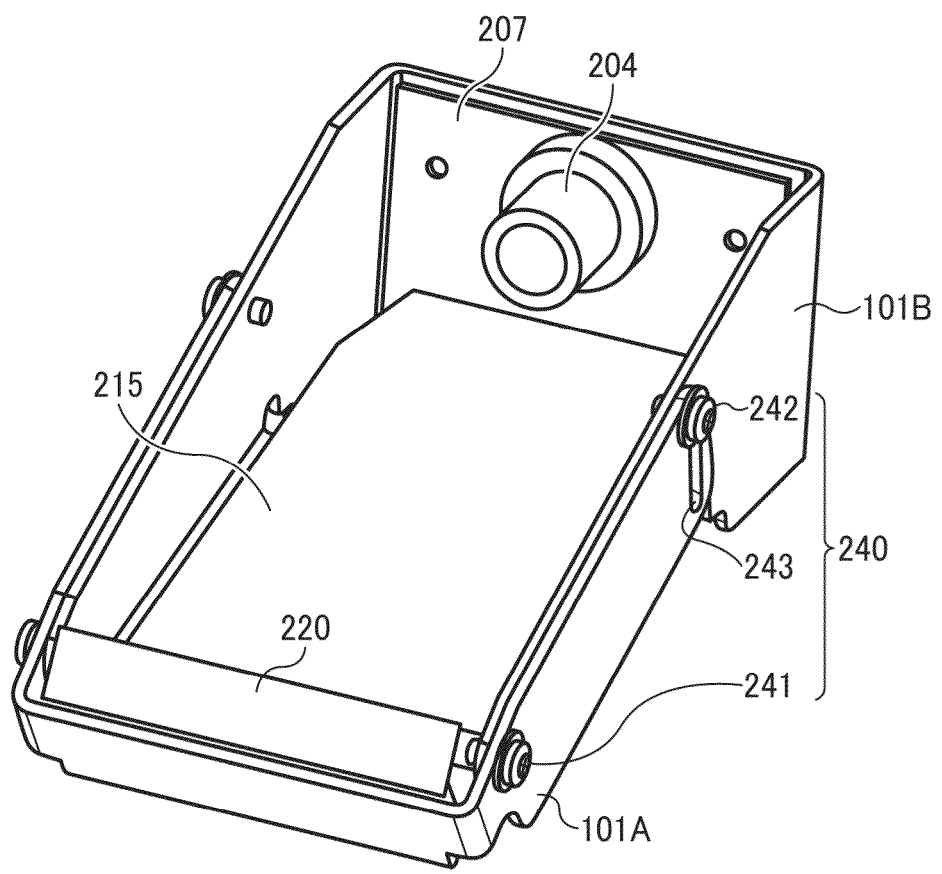
FIG. 8 is a perspective diagram illustrating as configuration of the image capturing unit.

FIG. 8 is a schematic perspective view illustrating a configuration of the image capturing unit 101. In this embodiment of the image capturing unit 101, the taper optical-path changing, member 215 shown in FIG. 6 is used as the optical-path changing member. In FIG. 8, the imaging unit 101 includes a first module 101A, serving as a first support member fixed to the inner surface of the windshield 105, which fixes and supports the reflection-polarization prism 220, and a second module 101A, serving as a second support member, which fixes and supports the sensor board 207 on which the image sensor 206 and LED 211 are mounted, the taper optical-path changing member 215, and the imaging lens 204.

These modules 101A and 101B are rotatable connected to each other by a rotation connection mechanism 240. The rotation connection mechanism 240 includes as rotary shaft 241 that extends in perpendicular to an inclined direction of the windshield 105 and a vertical direction, (front-back direction of paper on which FIG. 3 is drawn), fixing pin 242, and a guide hole 243. The rotation connection mechanism 240 rotates the first module 101A and the second module 101B in relative directions around the rotary shaft 241. The modules 101A and 101B are rotatably configured because, even when the first module 101A is fixed to the windshield 205 having as different inclined angle, the capturing direction of the image capturing device 200 in the second module 101B can be set to the a specified direction (e.g., horizontal direction in the present embodiment).

Herein, a setting process to set the image capturing unit 101 in the vehicle 100 is described below. Initially, the first module 101A is fixed to the windshield 105 so that the contact face 222 of the reflection-polarization prism 220 in the first module 101A closely contacts the inner surface of the windshield 105. At this time, for example, the first module 101A is attached to the windshield 100 by adhering to the windshield 100 or by engaging each other using a connection mechanism such as a hook fixed to the windshield 105 in advance.

Subsequently, the second module 101B is rotated around the rotary shaft 241 of the rotary connection mechanism 240 relative to the fixed first module 101A.

Then, an angle of the second module 101B is adjusted so that the capturing direction of the image capturing device 200 in the second module 101B is made in line with the horizontal direction, and then the second module 101B is fixed in an inner part of the vehicle 100.

In the present embodiment, the guide hole 243 formed in the first module 101A restricts a movable range of the fixing pin 242 fixedly provided to an outer surface of the second module 101B to limit a rotation adjusting range of the rotary connection mechanism 240, that is, to limit angle adjustment range of the second module 101B relative to the first module 101A. The rotation adjusting range of the rotary connecting mechanism 240 is appropriately set depending on the expected inclined angle range of the windshield 105. In the present embodiment, the inclined angle range of the windshield 105 is set approximately within the range between 20° and 35°; however, the inclined angle range can be changed depending on the types of vehicles that install the image capturing unit 101.

Figure 9A:
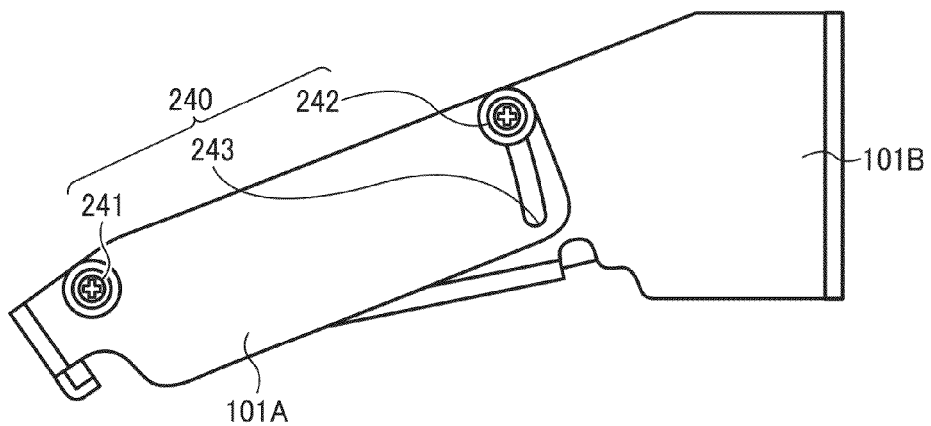
FIG. 9A is as side view illustrating the image capturing unit attached to the vehicle having the windshield with an inclination angle of 22 degrees relative to a horizontal plane.
Figure 9B:
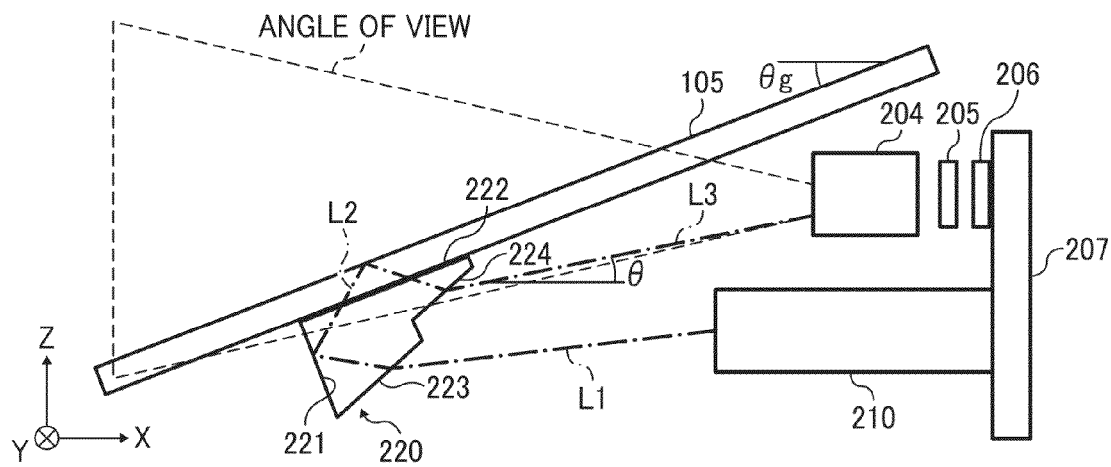
FIG. 9B is a diagram illustrating optical configuration of the image capturing unit when the raindrop is not present on the windshield shown in FIG. 9A.
Figure 9C:
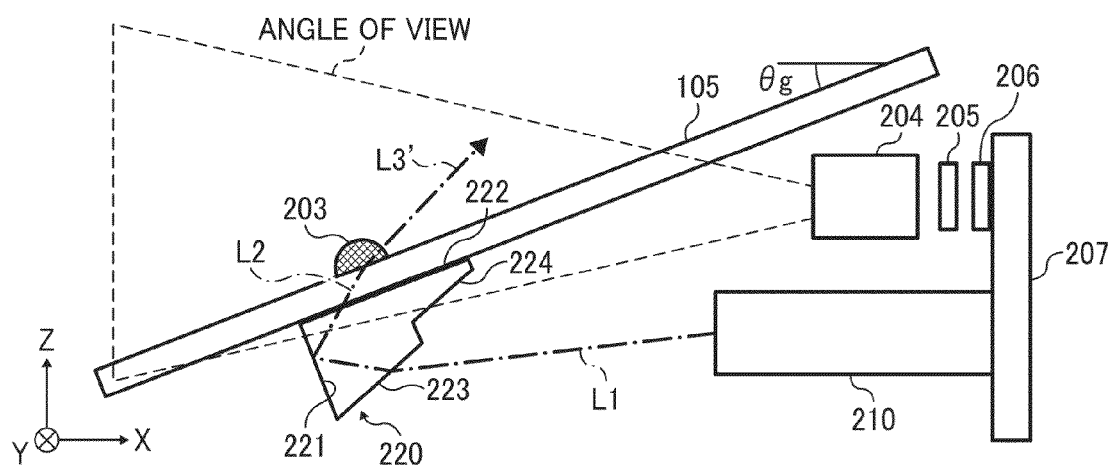
FIG. 9C is a diagram illustrating optical configuration of the image capturing unit when the raindrop is present on the windshield shown in FIG. 9A.

FIG. 9A is a side view illustrating the image capturing unit 101 attached to the vehicle 100 having the windshield 105 with an inclined angle θg of 22 degrees relative to a horizontal plane. FIG. 9B is a diagram illustrating optical configuration of the image capturing unit 101 when the raindrop is not present on the windshield 105 shown in FIG. 9A. FIG. 9C is a diagram illustrating optical configuration of the image capturing unit 101 when the raindrop 203 is present on the windshield 105 shown in FIG. 9A.

Figure 10A:
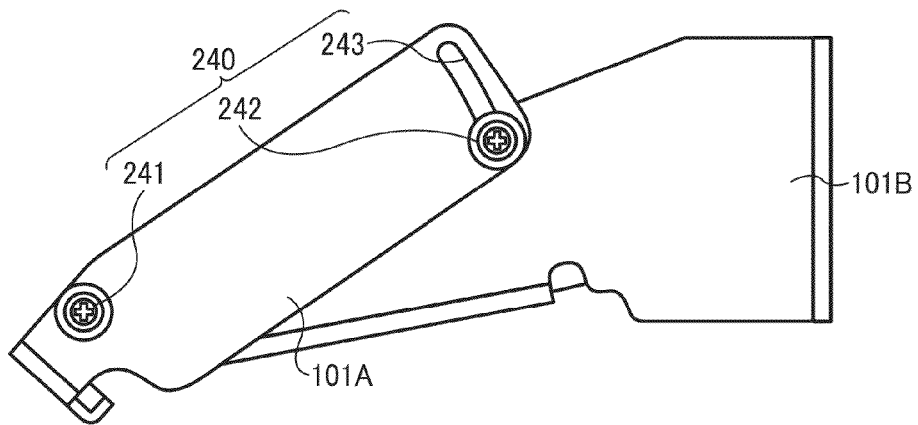
FIG. 10A is a side view illustrating the image capturing unit attached to the vehicle having the windshield with an inclination angle of 34 degrees relative to the horizontal plane.
Figure 10B:
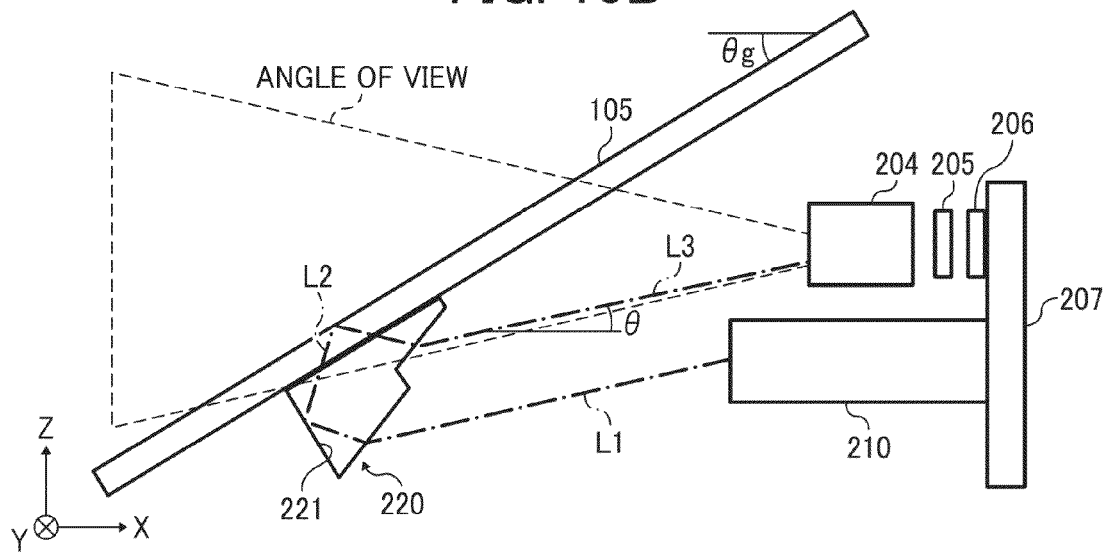
FIG. 10B is a diagram illustrating optical configuration of the image capturing unit shown in FIG. 10A.

FIG. 10A is a side view illustrating the imaging unit 101 attached to the vehicle 100 having the windshield 105 with an inclination angle θg of 34 degrees relative to the horizontal plane. FIG. 10B is a diagram illustrating optical configuration of the image capturing unit 101 shown in FIG. 10A.

A light L1 emitted from the light source 210 is regularly reflected from the reflection face 221 of the reflection-polarization prism 220 and then a reflected light L2 reflected from the reflection face 221 is transmitted through the inner surface of the windshield 105. When the raindrop is not present on the outer surface of the windshield 105, the reflected light L2 is totally reflected from the outer surface of the windshield 105. Then, a totally reflected light L3 reflected from the outer surface is penetrated through the inner surface of the windshield 105 and the penetrated light proceeds to the imaging lens 204. By contrast, when the raindrop 203 is present on the outer surface of the windshield 105, the reflected light L2 reflected from the reflection face 221 of the reflection-polarization prism 220 is penetrated through the outer surface of the windshield 105, and a penetrated light L3' proceeds outward.

With this configuration, when the inclined angle θg of the windshield 105 is changed, while the capturing direction of the second module 101B is kept in a state in which the capturing direction is fixed at the horizontal direction, the posture of the second module 101B fixed to the inner surface of the windshield 105 is changed, and the reflection-polarization prism 220 is rotated integrally with the windshield 105 around a Y axis direction.

Herein, the reflection face 221 of the reflection-polarization prism 220 is positioned relative to the outer surface of the windshield 105 so that the totally reflected light L3 from the outer surface of the windshield 105 is always received at a light receiving region (foreign substance detecting image region 232) of the image sensor 206 within the rotary adjustment range of the rotary connection mechanism 240, allowing detection of the condition change of the outer surface of the windshield 105.

According, even though the inclined angle θg of the windshield 105 is changed, the foreign substance detecting image region 232 of the image sensor 206 can receive the totally reflected light L3 from the outer surface of the windshield 105, which enables suitable raindrop detection.

In particular, the relative position is set so that Principle of Corner cube is substantially satisfied (a corner cube reflector rule is achieved) within the rotary adjustment range of the rotary connection mechanism 240. The corner cube reflector rule is the principle that, when two reflection faces are combined so as to form a right angle, and the light enters a first reflection face at an incident angle δ, the light reflected from the first reflection face is further reflected from a second reflection face and the light reflected from the second reflection face is output at an output angle δ at the same angle to the incident angle δ.

More specifically, when the light enters the first reflection face at the incident angle δ, the light is bent at an angle 2δ by reflection from the first reflection face. Then, when the light reflected from the first reflection face enters the second reflection face at an incident angle "90°−δ", the light bends at an angle "180°−2δ", reflection from the second reflection face.

By summing up these values, the formula holds, "2δ+180°−2δ=180°". Therefore, the light output from the second reflection face is returned to a direction in which the light comes to the first reflection face. In the present embodiment, since the relative position is set so that Principle of Corner cube is substantially satisfied within the rotary adjustment range in the rotary connecting mechanism 240, even when the incident angle θg of the windshield 105 is changed, the angle θ between the optical axis direction of the totally reflected light L3 from the outer surface of the windshield 105 and the horizontal direction is substantially kept constant. Accordingly, the fluctuation of an area through which the optical axis of the totally reflected light L3 from the outer face of the windshield 105 passes can be minimized in the foreign substance detecting image region 232 of the image sensor 206, which can detect suitable raindrop.

It is to be noted that, when the relative position is set so that the reflection face 221 of the reflection-polarization prism 220 is set in perpendicular to the outer surface of the windshield 105, the Principal of corner cube is satisfied. Alternatively, as long as the Principal of corner cube is substantially satisfied within the rotary adjusting range of the rotary connection mechanism 240, the relative position between the reflection face 221 of the reflection-polarization prism 220 and the outer surface of the windshield 105 with each other is not limited to the right angle. For example, although the reflection face 221 of the reflection-polarization prism 220 is not provided in perpendicular to the outer surface of the windshield 105, by adjusting angle of the other face (inputting face or exiting face 224) of the reflection-polarization prism 220, even when the inclined angle θg of the windshield 105 is changed, the angle θ of the optical axis of the totally reflected light L3 directed to the imaging lens 104 can be kept nearly constant.

For example, when the angle made by the reflection face 221 of the reflection-polarization prism 220 and the outer surface of the windshield 105 is set greater than 90°, by increasing the angle made by the exiting surface 224 of the reflection-polarization prism 220 and the contact face 222, the direction of the totally reflected light L3 can be kept nearly constant. At this time, it is preferable for the angle made by the exiting face 224 of the reflection-polarization prism 220 and the contact face 222 to increase to nearly twice the angle of an increased angle from 90° made by the reflection face 221 of the reflection polarized prism 220 and the outer surface of the windshield 105. In this case, although the exiting surface 224 of the reflection-polarization prism 220 is not in parallel to an entering surface (input surface) 223, by adjusting the angle of light output from the taper optical-path changing member 215 in accordance with the required exiting, angle from the reflection-polarization prism 220 to the imaging lens 204, this prism can be used.

In addition, in the configuration in which the Principle of Corner cube is substantially satisfied, an angle θ made by the optical axis direction of the totally reflected light L3 reflected from the outer surface of the windshield 105 and output from the exiting surface 224 and the horizontal plane can be substantially kept constant.

However, the outputting position of the totally reflected light L3 output from the reflection-polarization prism 220 is not always constant. By varying the outputting position, the area through which the optical axis of the totally reflected light L3 reaches the foreign substance detecting image region 232 of the image sensor 206 is changed, which may disturb the stable detection cal the raindrop 203.

In order to solve this problem, in the present embodiment, the position of the rotational center of the rotary connection mechanism 240 is contrived so that the optical axis direction of the totally reflected light L3 specularly reflected from the outer surface of the windshield 105 and output from the exiting surface 224 of the reflection-polarization prism 220 can reach a light receiving position within a predetermined light receiving range in the image sensor 206, in the rotary adjustment range of the rotary connection mechanism 240. More specifically, the position of the rotary shaft 241 of the rotary connection mechanism 240 is set so that the outputting position of the totally reflected light L3 output from the reflection-polarization prism 220 can be kept at a fixed position within a field of view of the image capturing device 200, in the rotary adjustment range of the rotary connection mechanism 240. For example, as one specific position, the rotary shaft 241 of the rotary connection mechanism 240 is positioned between a position at which the optical axis of the light L1 reaches the reflection face 221 of the reflection-polarization prism 220 and a position at which the optical axis of the light K2 reaches the outer surface of the windshield 105.

As described above, in the present embodiment, regardless of the inclined angle θg of the windshield 105, the installation process of the image capturing unit 101 is completed by using only two steps containing a fixing step to fix the first module 101A to the windshield 105 and an adjust-fixing process to adjust the angle of the second module 101B so that the capturing direction is made in line with the horizontal direction.

Figure 11:
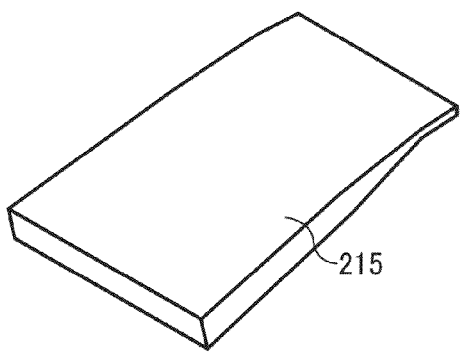
FIG. 11 is a perspective view illustrating a configuration of a taper optional-path changing member constituted by a taper rod lens.

FIG. 11 is a perspective view illustrating a configuration of the taper optical-path changing member 215. The taper optical-path changing member 215 is attached on the light source 210 side. A set of taper rod lenses constituted by a tubular mirror whose inner face functions as a reflection face may be used for an entrance side of the taper optical-path changing member 215. The taper optical-path changing member 215 has a taper shape that becomes wider from an entrance end surface to an exit end surface. The taper optical-path changing member 215 is made of material whose refractive index is equal to or greater than 1, such as glass. Since the taper optical-path Changing member 215 can be formed by molding, the taper optical-path changing member 215 can be made at the low cost.

Figure 12:
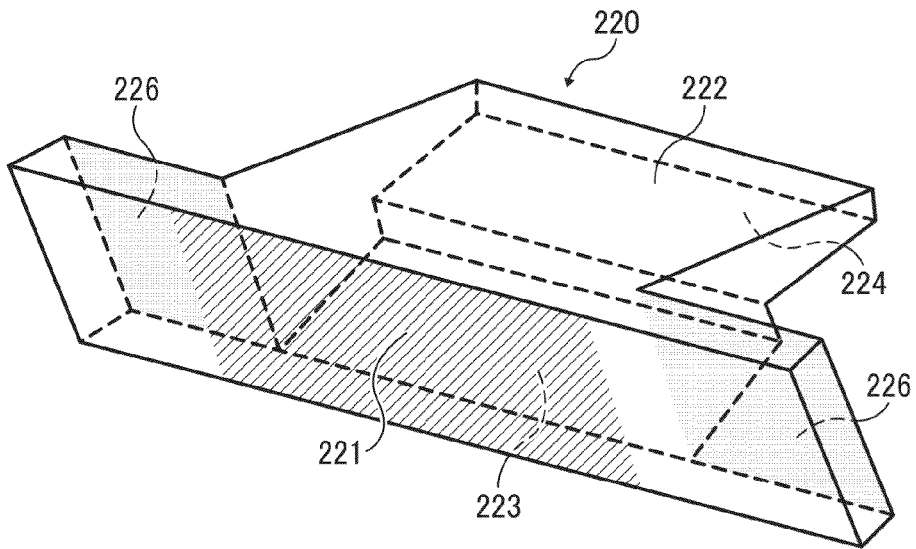
FIG. 12 is a perspective view illustrating a reflection-polarization prism in the image capturing unit shown in FIG. 3.

FIG. 12 is a perspective view illustrating the reflection-polarization prism 220 of the present embodiment. The reflection-polarization prism 220 is configured to be used, not only to detect the raindrop present on the outer surface of the windshield 105, but also to be used to detect fog on the inner surface of the windshield 105. More specifically, a center area (prism center area) of the reflection-polarization prism 220 in the Y-axis direction functions as an outer substance detector to detect the substances (raindrop, ice) present on the outer surface of the windshield 105. The side area (prism side area) of the reflection-polarization prism 220 in the Y-axis direction functions as an inner substance detector to detect the substances (fog) present on the inner surface of the windshield 105.

The prism center area of the reflection-polarization prism 220 includes the entering surface 223 to guide the light emitted from the light source 210 to enter the inside of the reflection-polarization prism 220, the reflection face 221 to reflect the light L1 passed through the entering surface 223, the contact face 222 provided in close contact with the inner surface of the windshield 105 to allow transmission the light L2 reflected from the reflection face 221 as a transmission face (transparent face), and the exiting face 224 to output the light L3 reflected from the outer surface of the windshield 105 to the image capturing device 200. In the present embodiment, although the entering surface 223 and the exiting surface 224 are provided in parallel with each other, the surfaces 223 and 224 may provided not in parallel.

The material of the prism center area of the reflection-polarization prism 220 may be formed of a material, capable of transmitting, at least the light emitted from the light source 210, such as, glass, or plastic. Since the light emitted from the light source 210 is an infrared light, the material of the reflection-polarization prism 220 is formed of a black or near black material that absorbs the visible light. By using the material that absorbs the visible light, it can suppress entering of the light other than the light (infrared light) from the LED 210 to the prism center area of the reflection-polarization prism 220.

In addition, the prism center area of the reflection-polarization prism 220 is formed so that a total reflection condition in which the light from the light source 210 is totally reflected from the reflection face 221 is established in the rotary adjustment area of the rotary connection mechanism 240. Alternatively, if it is difficult to establish the total reflection condition in which the light from the light source 210 is totally reflected from the reflection face 221 in the rotary adjustment area of the rotary connection mechanism 240, by evaporating an aluminum film on the reflection face 221 of the reflection-polarization prism 220, a reflection mirror may be provided.

In addition, in the present embodiment, although the reflection face 221 of the reflection-polarization prism 220 is a plane face, the reflection face 221 may be formed by a concave face. By using a concave-shaped reflection face, the diffusion luminous flux that enters the reflection face 221 can be set in parallel. With this configuration, the luminance degradation on the windshield 105 can be suppressed.

Figure 13:
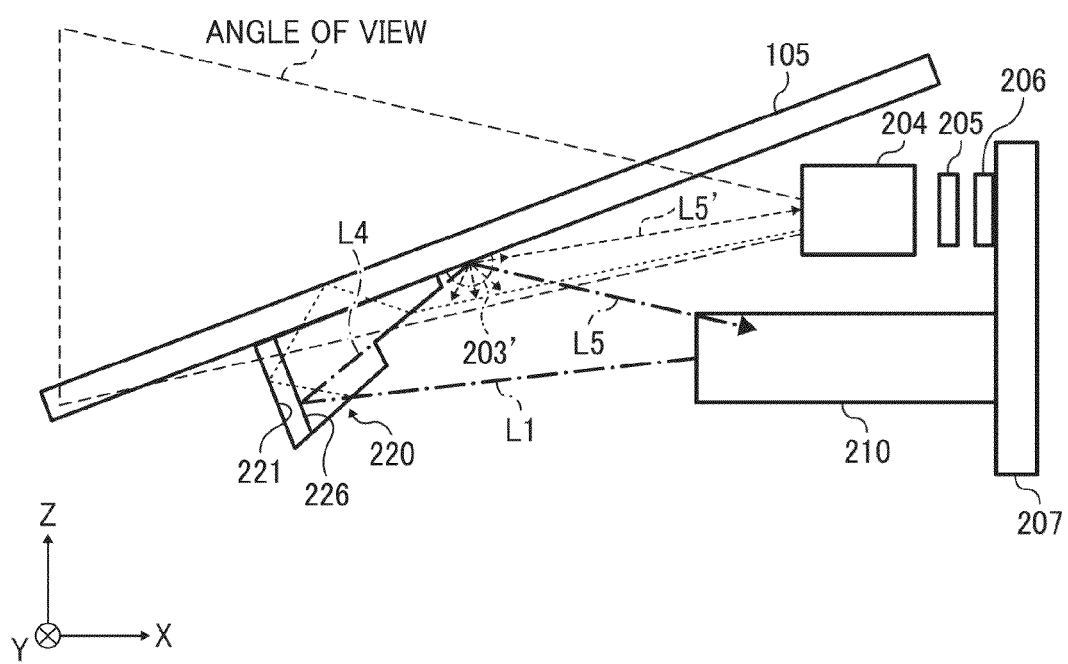
FIG. 13 is an optical configuration of the image capturing unit shown in FIG. 3 containing optical passing ways to detect the raindrop and the fog on the windshield.

FIG. 13 is an optical configuration of the image capturing unit 101 shown in FIG. 3 containing optical passing ways to detect the raindrop and the fog on the windshield 105. The prism end areas of the reflection-polarization prism 220 includes a reflection mirror face (light-guiding member) 226 as a light reflection member to reflect the light from the light source 210. Of the light emitted from the taper optical-path changing member 215, the tight positioned at the center area in the Y axis direction is emitted to the entering face 223 of the prism center area of the reflection-polarization prism 220 and then is totally reflected from the reflection face 221 and then is totally reflected from the outer non-substance detected area where the raindrop is not present on the outer surface of the windshield 105, and the light output from the exiting surface 224 is entered into the image sensor 206.

By contrast, the light positioned at the side areas in the Y-axis direction is not emitted to the entering face 223 of the reflection-polarization prism 220, but is totally reflected from the mirror face 226 positioned on the prism side ends of the reflection-polarization prism 220. The reflection light L4 is subjected to the inner surface of the windshield 105. When the fog is not present on the inner surface of the windshield 105, the reflection light L4 is reflected from the inner surface of the windshield 105. The specular reflected light L5 is configured so that the image sensor 206 does not always receive the light L5 reflected from the inner surface of the windshield 105 in the rotary adjustment range of the rotary connection mechanism 240.

When the fog is present on the inner surface of the windshield 105, the light L4 reflected from the mirror face 226 is diffusionally reflected from the foggy area on the inner surface of the windshield 105, and the image sensor 206 receives a diffusionally reflected light L5'. Accordingly, when a certain area in the image sensor 206 corresponding to the reflection mirror 226 receives over the defined amount of light reflected from the reflection mirror 226, the fog on the inner surface of the windshield 105 can be detected by receiving the diffusion reflected light L5' from the foggy area.

Herein, in the present embodiment, although the prism unit 222 that includes the reflection face 221 to detect the raindrop is integrally formed with the mirror unit 226 that includes the reflection mirror face (light-guiding member) 226 to detect fog, as one unit, the prism member and the mirror member may be formed independently. In addition, in the present embodiment, as illustrated in FIG. 12, while the mirror member 226 is positioned on both side areas of the prism member 220, the configuration is not limited above; alternatively, the mirror unit 226 is positioned on only one side of the prism unit 220 or is positioned a top or bottom of the prism unit 220.

In addition, in order to establish the total reflection condition of the reflection mirror surface 226, although the reflection mirror 226 is formed by evaporating the reflection fill such as aluminum on the reflection mirror 226, if the total reflection condition can be established only by the refractive index, forming the reflection film is not necessary.

Next, the optical filter 205 of the present embodiment is described below. When the raindrop on the outer surface of the windshield 105 and the fog on the inner surface of the windshield 105 are detected, the infrared light emitted from the light source 210 is captured by the image capturing device 200. At this time, the image sensor 206 in the image capturing device 200 may receive a great amount of disturbance (ambient) light containing infrared light such as the sunlight, in addition to the infrared light from the light source 210.

Accordingly, in order to discriminate the infrared light emitted from the light source 210 from the great amount of disturbance light, it is necessary to set the amount of emitting light of the light source 210 at a value greater than the value of disturbance light. However, it is commonly difficult to use the light source 210 that emits such a great amount of light.

Figure 14:
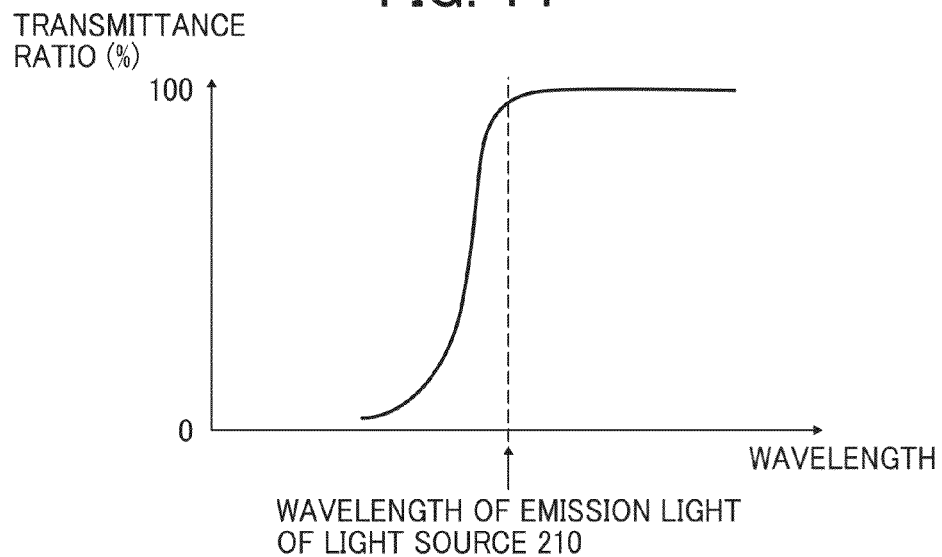
FIG. 14 is a graph illustrating filter characteristics of a cut filter used for detecting the foreign substance in captured image data.
Figure 15:
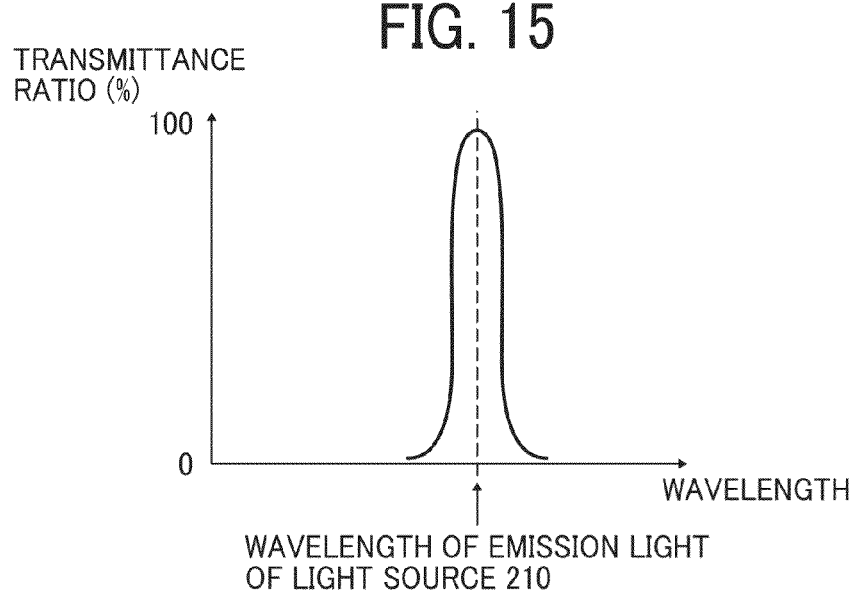
FIG. 15 is as graph illustrating filter characteristics of a band-pass filter used for detecting the foreign substance in the captured image data.

In order to solve this problem, a cut filter to cut the light whose light emitting wavelength is shorter than that of the light source 210 is used as illustrated in FIG. 14. Alternatively, a band-pass filter with a transmission peak having a wavelength nearly coincidence with the light emitting wavelength of the light source 210 is used as illustrated in FIG. 15. Using the filter, the light other than the infrared light emitted from the light source 210 is eliminated, and the image sensor 206 receives the eliminated light. With this configuration, the amount of light from the light source 210 received at the image sensor 206 becomes relatively greater than the great amount of disturbance light. As a result, even though the light source 200 that emits the great amount of light is not used, the light emitted from the light source 210 can be discriminated from the great amount of disturbance light.

Herein, based on the captured image data, the image sensor 206 detects not only the raindrop and the fog on the windshield 105, but also the leading vehicle and the oncoming vehicles. Therefore, if the wavelength band other than the infrared light emitted from the light source 210 is eliminated in the entire captured image, the light having the wavelength range needed for detecting the leading vehicle and the oncoming vehicle and the white line cannot be received, which may adversely effect on detection of the leading vehicle and the oncoming vehicle and the white line.

In order to solve this problem, the image area of the captured image data is divided into the foreign substance detecting image region 232 for detecting the foreign substance such as raindrop and fog on the windshield 105 and a vehicle detecting image region (capturing image receiving region) 231 to detect the leading vehicle, the oncoming vehicle, and the white line. Then, the optical filter 205 has a filter that eliminates the wavelength range other than the infrared light emitted from the light source 210 is provided only on an area corresponding to the foreign substance detecting image region 232.

Figure 16:
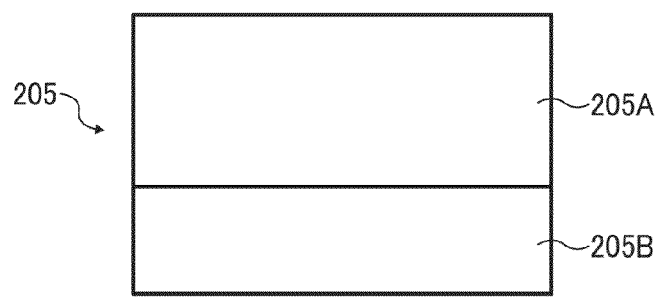
FIG. 16 is a front view illustrating the optical filter, included in the image capturing unit, that is divided into a vehicle detection filter corresponding to a vehicle detecting image region and a foreign substance detection filter corresponding to a foreign substance detecting image region.
Figure 17:
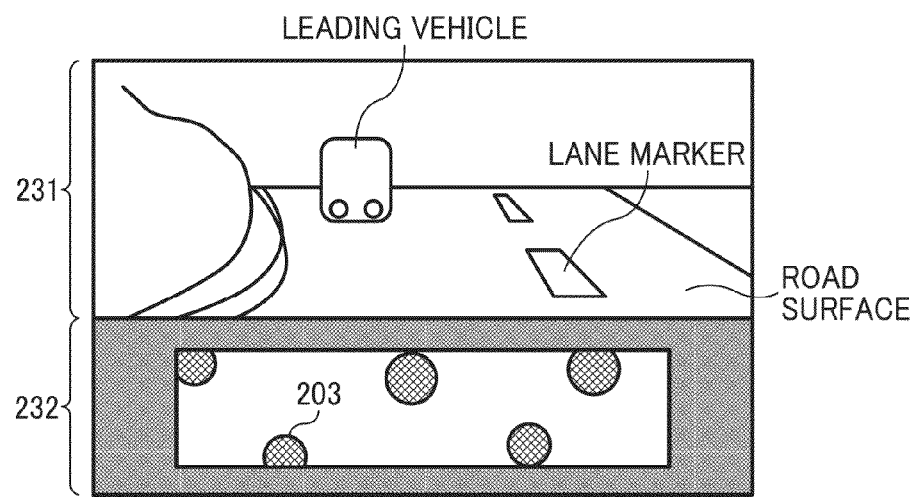
FIG. 17 is an illustration of example image of the captured image data.

FIG. 16 is a front view illustrating the optical filter 205 that is divided into a vehicle filter area 205A corresponding to the vehicle detecting image region 231 (shown in FIGS. 17 and 19) and a substance filter area 205B corresponding to the foreign substance detecting image region 232. FIG. 17 is an illustration of example image of captured image data. As illustrated in FIG. 17, the vehicle detecting, image region 231 corresponds to the upper two third in the captured image, and the foreign substance detecting image region 232 corresponds to the lower one third of the captured image. The vehicle targets such as head light of the oncoming vehicle, tail light of the leading vehicle, white line, and road sign are often positioned upper area in the captured image. The near load of the area ahead of the vehicle 100 and hood of the own vehicle 100 are presented.

Accordingly, the information needed for identifying the head light of the oncoming vehicle, the tail light of the leading vehicle, white line, and road sign is concentrated on the upper area in the captured image, and the information in the lower area in the captured image may not be necessary. With this situation, using a single captured image data, while the oncoming vehicle, the leading vehicle, the white line, and the road sign are detected, the foreign substances such as raindrop and fog can be detected at the same time as illustrated in FIG. 17. In this case, it is preferable that the to lower area of the captured image 23 be set as the foreign substance detecting image region 232 and the remained upper area of the captured image be set as the vehicle detecting image region 231, and the optical filter 205 be divided into areas that respectively correspond to the foreign substance detecting region 232 and the vehicle detecting image region 231.

In addition, the hood of the vehicle 100 be appeared in the lower area of the captured image. In this case, the sunlight reflected from the hood of the vehicle 100 and the tail light of the leading vehicle may become disturbance light, and containing the disturbance light in the capture image data causes the error recognition of the head light of the oncoming vehicle, the tail light of the leading vehicle, and white line.

In this case, in the present embodiment, since the cut filter FIG. 14 or the band-pass filter shown in FIG. 15 is attached to the area corresponding to the lower area in the captured image, the sunlight reflected from the hood and the disturbance light in the tail light of the leading vehicle are eliminated. Accordingly, the recognition accuracy of the head light of the oncoming vehicle, the tail light of the leading vehicle, and the white line is improved.

The optical filter 205 has a different layer configuration each for the vehicle detection filter 205A corresponding to the vehicle detecting image region 231 and the foreign substance detection filter 205B corresponding to the foreign substance detecting image region 232. More specifically, the vehicle detection filter 205A does not include a spectral filter layer 251, but the foreign substance detection filter 205B includes the spectral filter layer 251. In the present embodiment, due to the characteristics of the image lens 204, the scenery of the captured image data is appeared upside down from the image on the image sensor 206. Accordingly, when the lower area in the captured image is set to the foreign substance detecting image region 232, the upper area of the optical filter 205 is configured to the foreign substance detection filter 205B.

Herein, in the process of detecting the leading vehicle, the leading vehicle is detected by identifying the tail light in the captured image. The tail light has a fewer amount of light than the head light, and there is much disturbance light such as street lamp, such that it is sometimes difficult to detect the tail light with a high degree of accuracy by only using luminance data. In this case, by using the spectral information for identifying the tail light and identifying the tail light based on the amount of receiving light of the red light, the recognition accuracy of the tail light can be improved. Accordingly, by providing a red filter or a cyan filter (that transmits only a light having a specified wavelength band corresponding the tail lamp color) in the optical filter 205, and the amount of receiving light of the red light may be detected.

Since the respective light receiving elements constituting, the image sensor 206 has certain sensitivity to the infrared wavelength band light, if the image sensor 206 receives the light containing the infrared wavelength hand, the acquired captured image becomes reddish in whole. As a result, identifying the read image area corresponding to the tail light is sometimes difficult. In order to solve this problem, the optical filter 205 includes a spectral filter layer 255 to cut a light having a visible light area to the light source wavelength area (see FIG. 20).

Figure 18:
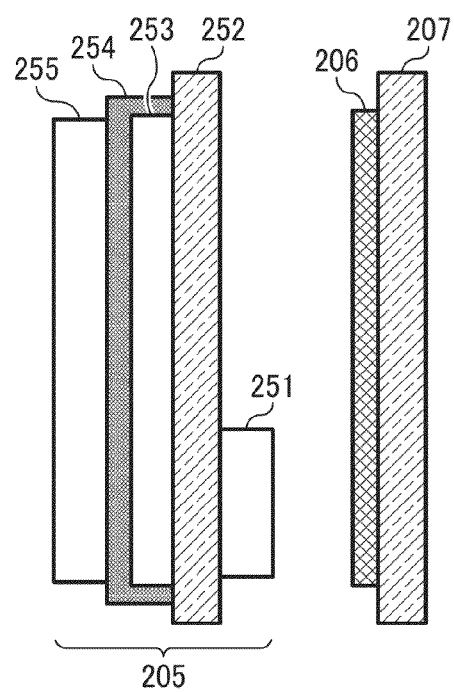
FIG. 18 is a schematic expanded view of the optical filter and the image sensor when viewed from a direction in which the light passes.
Figure 19:
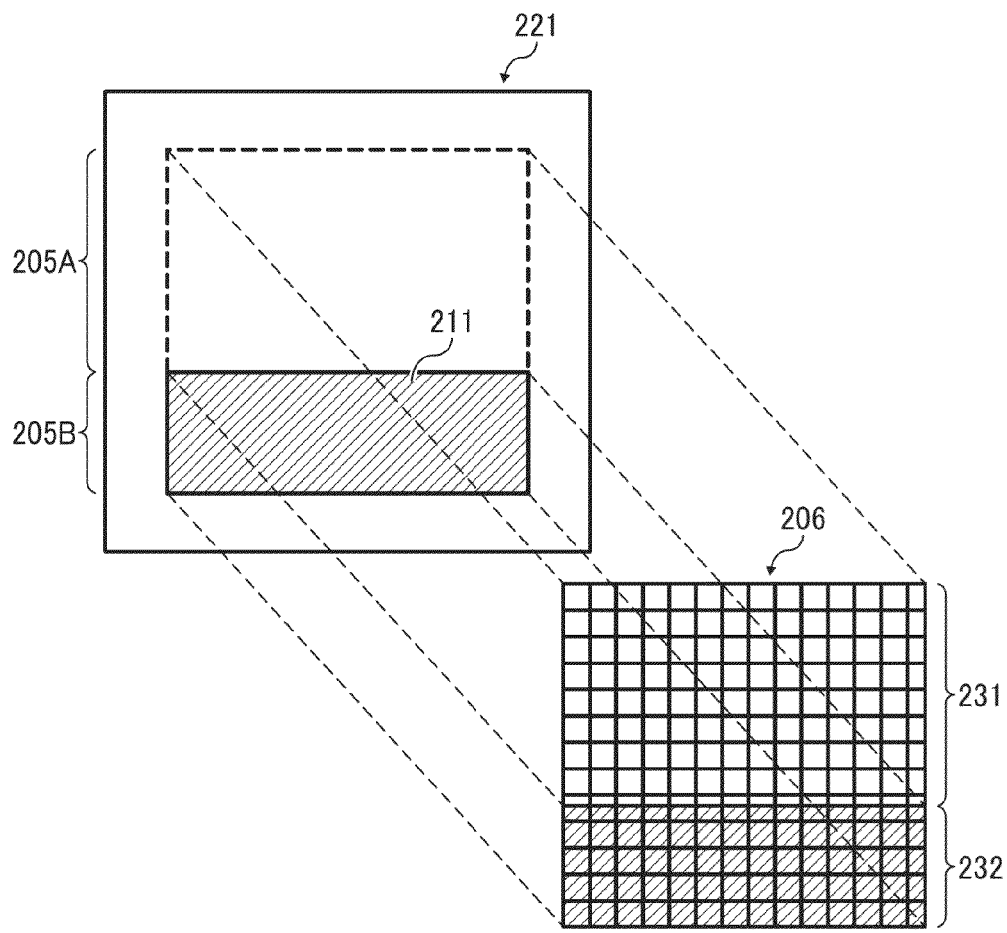
FIG. 19 is a relative position illustration showing the vehicle detection filter of the optical filter corresponding to the vehicle detecting image region of the image sensor, and the foreign substance detection filter in the optical filter corresponding, to the foreign substance detecting image region in the image sensor.

FIG. 18 is a schematic expanded view of the optical filter 205 and the image sensor 206 when viewed from a direction in which the light passes. FIG. 19 is a relative position illustration showing the vehicle detection filter 205A of the optical filter 205 corresponding to the vehicle detecting image region 231 in the image sensor 206, and the foreign substance detection filter 205B in the optical filter 205 corresponding to the foreign substance detecting image region 232 in the image sensor 206.

The optical filter 205 is provided adjacent to at receiving face of the image sensor 206. As illustrated in FIG. 18, the optical filter 205 is formed by forming the spectral filter layer 255 on one face (position facing to the light-receiving face of the image sensor 206) of the clear filter substrate 252 and forming a polarizing filter layers 253 and spectral filter layers 255 in series on the other face of the clear filter substrate 252. The optical filter 205 is attached to the image sensor 206 using, for example, a UV adhesive. Alternatively, four sides other than the effective pixels of the filters and the image sensors may be connected using UV adhesive or by heat, while the four sides other than the effective pixel range used for capturing an image is being supported by a spacer.

Herein, the optical filter 205 is further described below. The filter substrate 252 of the optical filter 205 is formed by a clear material such as glass, sapphire, crystal, that can transmit the light in the use range (in the present embodiment, the visible light area and the infrared light area). In the present embodiment, it is desirable that the filter substrate 205 be made of a glass, in particular, a silica glass (refractive index 1.46) that is inexpensive and have high durability, and TEMPAX® glass (refractive index 1.51).

Figure 20:
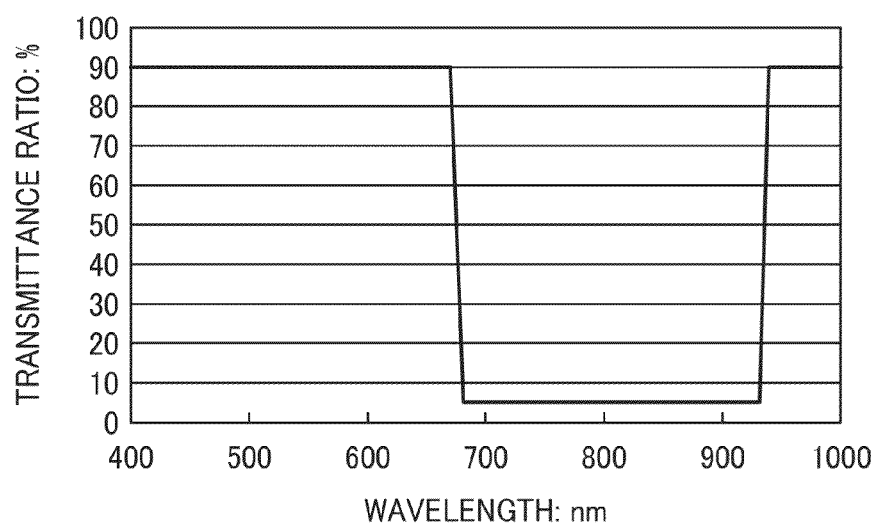
FIG. 20 is a graph illustrating transmissive characteristics in a first spectral filter layer in the optical filter.

FIG. 20 shows transmittance characteristics of the spectral filter layer 255 of the optical filter 205. In FIG. 20, the spectral filter layer 255 has the following transmittance characteristics. The spectral filter layer 255 transmits the incident light within a visible light area having a wavelength range between 400 am and 670 nm and within an infrared light area having a wavelength range between 940 nm and 970 nm and cuts the incident light within the wavelength range greater than 670 nm but less than 940 nm. The transmittance of the light of wavelength range between 400 nm and 670 nm and between 940 nm and 970 nm is equal to or greater than 30%. In particular, it is preferable that the transmittance in this area be set equal to or greater than 90%. The transmittance of the light of wavelength range greater than 670 nm but less than 940 nm is equal to or smaller than 20%. In particular, it is preferable that the transmittance in this area be set equal to or smaller than 5%.

The incident light of the visible light area is used to detect the vehicle and the white line in the vehicle detecting image region 231, and the incident light of the infrared light area is used to detect the foreign substances (raindrop, fog) of the windshield 105 in the foreign substance detecting image region 232. The reason why the incident light of the wavelength range greater than 670 nm but less than 940 nm, is that, if the waveform range greater than 670 nm but less than 940 nm is taken, the acquired image data becomes entirely reddish, and extracting the area indicating the red such as tail light and read color sign becomes difficult. In the present embodiment, the incident light of wavelength range greater than 670 nm but less than 940 nm is cut by the spectral filter layer 255. With this configuration, the recognition accuracy of the tail light is improved, and the detection accuracy of the road sign containing the red such as stop sign in Japan is improved. It is to be noted that, the wavelength range between 940 nm and 970 nm and between 400 nm and 670 nm is just one typical example of the present embodiment.

The spectral filter layer 255 has a multi-layer structure in which thin films having high refractive index and thin films having low refractive index are alternately superimposed. With this multi-layer structure, using light interference, flexibility in setting the spectral transmittance increases. By superimposing the multiple thin films, almost 100% reflection rate relative to a certain wavelength (e.g., the wavelength other than infrared light) can be established.

The polarizing filter layer 253 of the optical filter 205 is provided for alleviating the noise caused by unnecessary reflection light. The light emitted from the light source 210 is reflected from the inner surface and the outer surface of the windshield 105, and then the reflected light enters the image capturing device 200. In this reflection light, a polarization component (horizontal polarization component) in perpendicular to a plane (e.g., vertical plane) formed by the optical axis of the light emitted to the windshield 105 of the light source 210 and the optical axis of the light emitted to the imaging lens 204 is intense. Accordingly, the polarizing filter layer 253 is configured by a polarizing filter through which the horizontal polarization component is transmitted and a vertical polarization component in parallel to the vertical face is cut.

Figure 21:
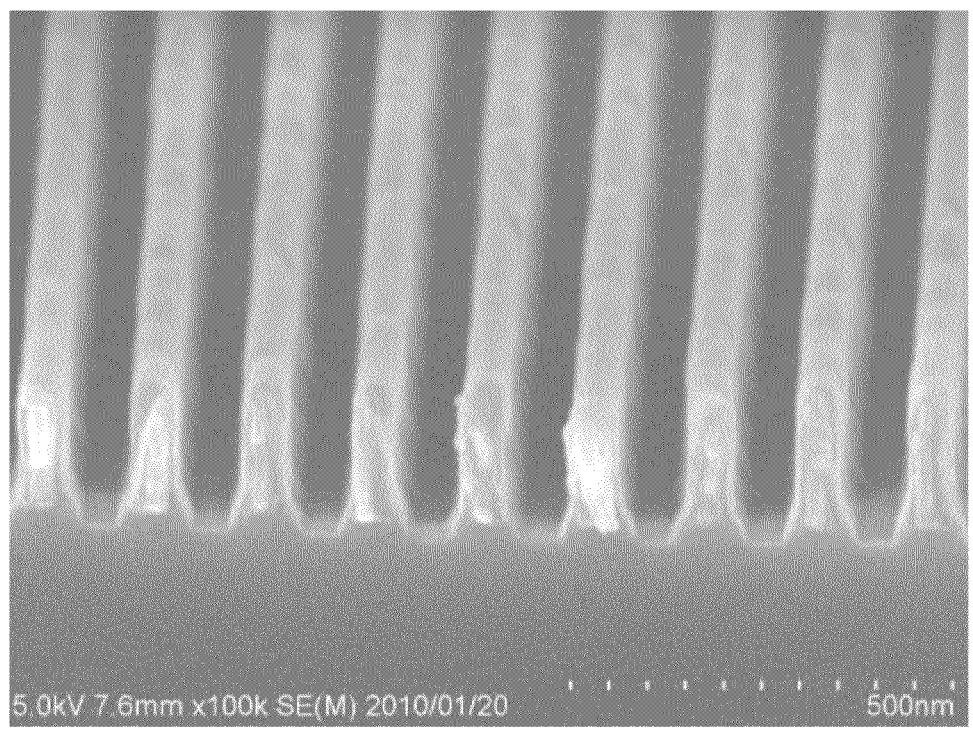
FIG. 21 is an expanded diagram illustrating a wire-grid polarizer constituting a polarized fitter layer in the optical filter.

As illustrated in FIG. 21, the polarizing filter layer 253 is constituted by a wire grid polarizer. The wire grid polarizer is formed by arranging conductive lines formed of metal such as aluminum at a specified pitch in a grid-like formation. As long as the arranged pitch is far smaller than (e.g., smaller than one-half of) the wavelength of the incident light visible light wavelength), the light of the electrical filed vector component that vibrates in directions parallel to the conductive lines is almost reflected, and the light of the electrical filer vector component that has vertical electrical vectors relative to the conductive lines can be transmitted, then the wire grid polarizer can be used as a polarizer to form a single polarization.

It is to be noted, that, in the wire grid, polarizer, if the cross-sectional area of the metal wire is increased, an extinction ratio is increased, and the transmittance is decreased in the metal wire having greater than the certain width relative to the cycle width. In addition, when the cross-sectional shape in perpendicular to a longitudinal direction of the metal wire is taper shape, the transmittance and the wavelength dispensability of the polarization in the width band is few, which indicates high extinction ratio characteristics. Further, the structure of the wire grid is formed by a known semiconductor process, such as, after the aluminum thin film is evaporated, a metal edging is performed by patterning. Using this process, sub wavelength convex concave structure of the wire grind is formed. Accordingly, the direction of the polarizer can be adjusted at a pixel size of the imaging elements (several micron levels). In addition, the wire grid polarizer is made from metal such as aluminum, which has high heat-resistance, which is suitable for installation in a car.

A filling layer 254 is formed by infilling an inorganic material whose refractive index is equal to or lower than the filter substrate 252 in a clearance between the filter substrate 252 and the polarizing filter layer 253 and in a clearance, among the wire grid convex areas. In order not to degrade the polarized characteristics of the polarizing filter layer 253, it is desirable that the filler layer 254 be formed of a material whose refractive index is close to that of the air as much as possible. For example, porous ceramics material in which fine holes are dispersed in the ceramics is preferable, which is made of, for example, porous silica ($SiO_2$), porous magnesium fluoride (MgF), and porous aluminum oxide ($Al_2O_3$). In addition, how low of the refractive index it is determined by the size (porous silica) of the holes in the ceramics. That is, in particular, the filter substrate 252 is mainly formed of silica crystal and glass, when the infill layer 253 is formed of porous silica (n=1.22 to 1.26), which is preferable because the refractive index of the porous silica becomes smaller than the filter substrate 252.

The filler layer 254 is formed by Inorganic material coating film (spin on glass: SOG) method. That is, a solvent in which a Silanol ($Si(OH)_4$) is dissolved with alcohol spin coated on the filter substrate 252, and the solvent component is volatilized by heat treatment, and the Silanol is dehydrated and polymerized, which forms the filler layer 254.

Since the polarizing filter layer 253 has a wire grid configuration of sub wavelength size, the polarizing filter layer 253 has low intensity, compared to the spectral filter layer 255 that is formed on the filler layer 254. In the present embodiment, since the filler layer 254 covers the polarizing filter layer 253 having low intensity, it is less likely to damage the wire grind structure of the polarizing filter layer 253 when the optical filter 205 is mounted. In addition, by providing the filler layer 254, entering foreign substance to the wire grid structure of the polarizing filter layer 253 can be inhibited.

The height of the concave portion of the wire grid of the polarizing filter layer 253 is generally set equal to or lower than half of the use wavelength. By contrast, the spectral filter layer 255 has a height equal to or several times of the use wavelength, and the transmittance characteristics can be rapidly changed in a shield wavelength as the thickness is increased. Alternatively, as the thickness of the filler layer 254 is increased, ensuring the flatness characteristics of the upper face of the filler layer 254 becomes difficult and the homogeneity is impaired. Therefore, increasing thickness is not desirable.

In the present embodiment, after the polarizing filter layer 253 is covered with the filler layer 254, the spectral filter layer 255 is formed. With this process, the filler layer 254 can be stably formed. The spectral filter layer 255 can be formed on the filler layer 254 so that the characteristics of the spectral filter layer 255 can be effectively used.

In the present embodiment, the spectral filter layer 255, the filler layer 254, and the polarizing filter layer 253 are arranged on the imaging lens 204 side with respect to the filter substrate 252. In general, compensating the disadvantage of the manufacturing process of the respective layers is important, the allowable limit of the fault size is increased as the target layers (255, 254, and 253) are apart from the imaging sensor 206. The filter substrate 252 has a thickness range between 0.5 mm and 1 mm. In the present embodiment, the manufacturing process can be simplified, which can reduce the manufacturing cost, compared to the case in which the respective layers (255, 254, and 253) are arranged on the image sensor 206 side.

Further, in the present embodiment, the spectral filter layer 251 is formed on the image sensor 206 side relative, to the filter substrate 252. The spectral filter layer 251 is provided only on the foreign substance detection filter 205B and is not provided on the vehicle detection filter 205A. As described above, if the light of the infrared wavelength reflected from the droplet and the ice on the windshield 105 is to be directly detected, the light source 210 that emits the infrared wavelength light must be set that emitted light be brighter than the disturbance light that has enormous amount of light such as sunlight, which is a problem.

In order to solve this problem, the spectral filter layer 251 constituted by as filter that cuts a light having the wavelength shorter than the emission wavelength of the light from the light source 210 or the band-pass filter whose wavelength is almost coincident with the emission wavelength of the light.

Figure 22:
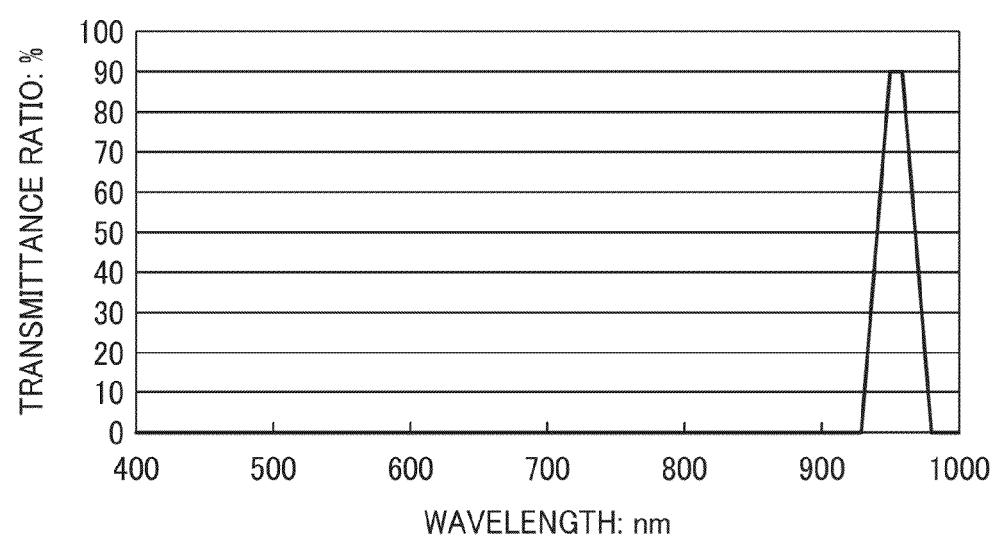
FIG. 22 is a graph illustrating transmissive characteristics in a second spectral filter layer in the optical filter.

As one example, the spectral filter layer 251 is constituted by the band-pass filter whose transmittance peak is almost coincident with the emission wavelength of the light, as illustrated in FIG. 22. With this configuration, the disturbance light other than the emission wavelength of the light from the light source is removed, and the detected amount of light from the light source 210 is relatively increased.

The optical filter 205 includes two spectral filter layers 251 and 255 and the spectral filter layer 251 is provided on one face of the filter substrate 252, and the spectral filter layer 255 is provided on the other face of the filter substrate 252. With this configuration, warpage of the optical filter 205 can be restricted. If the multi-layer film is formed on only one face of the filter substrate 252, the filter substrate 252 is warped by applying the stress from one side. By contrast, when the multi-layer film is formed on both faces of the filter substrate 252, the stress effect is got balanced out, thereby preventing the warpage.

The spectral filter layer 251 has multi-layer film structure. The multi-layer film means a wavelength filter in which a thin film of high refractive index and a thin film of low refractive index are alternatively superimposed. Using the interference of the light, the spectral transmittance can be freely set, and by superimposing a great number of films, almost 100% reflection rate for the specified wavelength can be satisfied. Herein, by providing a mask while the multi-layer film 205A is evaporated, and the filter 205 is evaporated while the vehicle detection filter area 205A is shielded. Using this process, the spectral filter layer 251 can be formed on the foreign substance detection filter 205B so as not to form the spectral filter layer 251 on the vehicle detection filter 205A.

In the present embodiment, since the spectral filter layers 251 and 255 have the multi-layer film structures, arbitrarily spectral luminance characteristics can be acquired. In general, the color filter generally used for color sensor is formed of resist developer (photosensitive material). However, the resist developer is difficult for controlling the spectral luminance characteristics, compared to the multi-layer film. In the present embodiment, by using the multi-layer film structure, the transmission wavelength range of the optical filter layers 251 and 255 can be almost coincident with the wavelength range of the light source 210.

In the present embodiment, although the spectral filter layer 251 is provided for restricting the disturbance light, the configuration is not limited above. Without the spectral filter layer 251, the raindrop can be detected. However, it is a favorable configuration in which the adversely effect of the disturbance light is removed in this embodiment because the noise does not fluctuate in detecting the raindrop and fog.

Figure 23A:
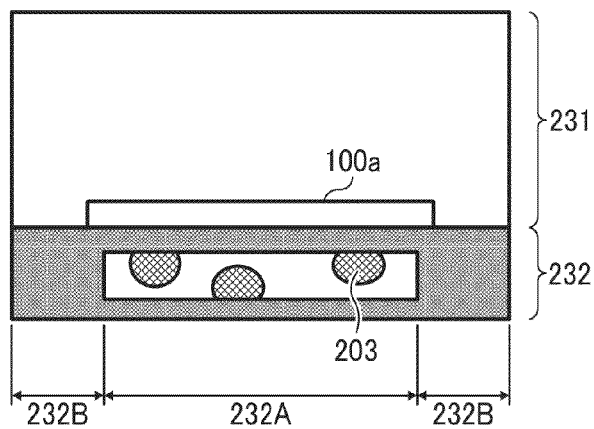
FIG. 23A is an illustration of one example of captured image captured when the state in which raindrop is present and fog is not present on the windshield, using the reflection-polarization prism shown in FIG. 12.
Figure 23B:
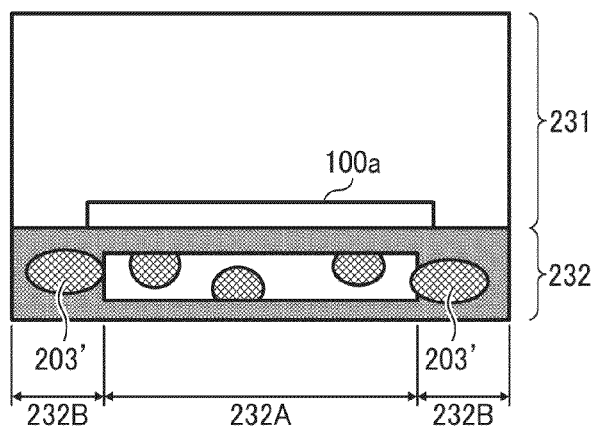
FIG. 23B is an illustration of one example of captured image when the state in which both raindrop and fog are present on the windshield, using the reflection-polarization prism shown in FIG. 12.

FIG. 23A is an illustration of one example of captured image captured when the raindrop is present but fog is not present on the windshield 105 using the reflection-polarization prism 220 of the present embodiment shown in FIG. 12. FIG. 23B is an illustration of one example of captured image captured when both raindrop and fog are present on the windshield 105 using the reflection-polarization prism 220. When the reflection-polarization prism 220 is used, a central region in a horizontal direction (raindrop detection region, first light receiving member) 232A in the foreign substance detecting image area 232 receives the light L3 regularly reflected from the outer non-substance detected area where the raindrop 203 is not present on the outer surface of the windshield 105, in the light L1 emitted from the light source 210, the central region 232A has high luminance in the area receiving the light L3 from the outer non-substance detected area. In addition, in the central region 232A of the foreign substance detecting, image region 232, the amount of receiving light L3', regularly reflected from the outer substance detected area where the raindrop 203 is present on the outer surface of the windshield 105, is decreased in the light L1 emitted from the light source 210, the central region 232A has low luminance in the area receiving the light L3' from the outer substance detected area.

On the other hand, when the fog does not form on the inner surface of the windshield 105, the both end regions 232B of the foreign substance detecting image region 232 does not receive the light L5 emitted from the light source 210 and regularly reflected from the inner surface of the windshield 105, and the spectral, filter layer 251 cuts the disturbance light. At this time, the both end regions 232B have low luminance. However, when the inner surface of the windshield 105 fogs up, it is regarded as the situation in which minuscule droplet of water forms on the inner surface of the windshield 105, and the both end regions 232B receive the diffusely reflected light L4'. As a result illustrated in FIG. 23B, in the both end regions 232B, the area corresponding to the foggy area 203' has higher luminance than that corresponding to the area where the fog does not form In addition, when the inner surface of the windshield 105 is fogged, an outline (edge) of a hood 100a shown in the vehicle detecting image region 231 becomes fuzzy when shown. Using this characteristic, whether fog forms or not can be detected.

Herein, even in a configuration in which the optical filter 205 is provided, since there is the disturbance light that is transmitted through the band-pass range of the optical filter 205 (external light having the wavelength equal to the emission of the light source 210), the influence of the disturbance light cannot be completely eliminated. For example, in daytime, the infrared wavelength component contained in sunlight affects the detection as the disturbance light. In nighttime, the infrared wavelength component contained in the head light of the oncoming vehicle affects the detection as the disturbance light. When these disturbance lights are present, detection error may arise when the raindrop 203 and the fog 203' are detected.

For example, as an algorithm to detect the raindrop 203 and the fog 203', when the algorithm that determines that the raindrop 203 and the fog 203' are present on the area where the luminance is changed over a predetermined value in the foreign substance detecting image area, the luminance is offset due to the disturbance light, which may generate the error detection of the raindrop 203 and fog 203'.

In order to prevent the error detection, for example, lighting in the light source 210 is controlled in synchronization with the exposure timing of the image sensor 206. More specifically, the captured image when the light source 210 is lighted up and the captured image when the light source 210 is switched of are acquired, and a differential image is generated between the two captured images for the foreign substance detecting image region 232, and the raindrop and the fog are detected based on the differential image. Accordingly, in order to detect the raindrop and the fog using this method, at least two-framed captured images are used.

Figure 24A:
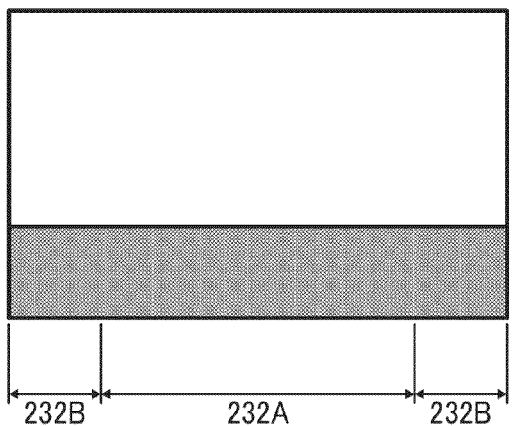
FIG. 24A is an illustration of the captured image when the light source is switched of to detect raindrop in one of two frames.
Figure 24B:
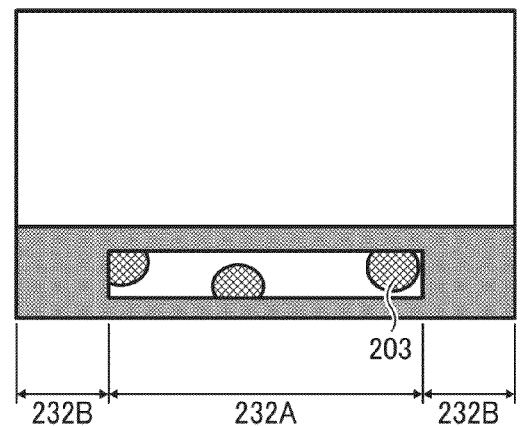
FIG. 24B is an illustration of the captured image when the light source is switched on to detect raindrop in the other of two frames.

One of the two frames to detect the raindrop and the fog is acquired in a state in which the light source 210 is lighten up as illustrated in FIG. 24A, and the other is acquired in a state in which the light source 210 is switched off as illustrated in FIG. 24B. In FIG. 24A, the illustration of the foreign substance detecting image region 232 acquired when the light source 210 is switched off shows only the disturbance light. By contrast, FIG. 24B, the illustration of the foreign substance detecting image region 232 acquired when the light source 210 is lighted up shows the light containing the disturbance light and light emitted from the light source 210. With this setting, the luminance value (pixel value of the differential image) acquired by calculating the luminance difference between the two frames shows the value from the disturbance light is eliminated. Accordingly, by detecting the raindrop and the fog based on the differential image, the error detection caused by the disturbance light can be restricted. Herein, at the time other than the timing at which the light source 210 is light up to detect the raindrop and the fog, turning off the light source 210 is suitable for saving energy.

In the disturbance light, the sunlight is not greatly changed even after a short period of time has elapsed, the head light of the oncoming vehicle while moving the vehicle 100 is changed even when the short time has elapsed. In this case, if an interval between the two frames to acquire the differential image is long, the amount of the disturbance light is changed, and when the differential image is generated, the disturbance light cannot be appropriately cut. In order to prevent this case, it is desirable that the two frames to detect the differential image be continuous frames.

In addition, when the vehicle and light distribution are controlled based on the image information of the vehicle detecting image region 231, automatic exposure control (AEC) is generally performed in accordance with the luminance in the center area of the captured image. However, it is desirable to have exposure of the light source 210 be controlled to optimally detect the raindrop and the fog for the two frames to detect the raindrop and the fog. This is because, if the automatic exposure control is performed when capturing images in the two frames to detect the raindrop and the fog, the exposure time may be changed between the frame when the light source 210 is lighted up and the frame when the light source 210 is switched off. If the exposure time is changed between the two frames, the luminance values of the disturbance light contained in the frames are changed, and the disturbance light may not be accurately eliminated by using differential image. In order to solve this problem, exposure is controlled so that the exposure times for the two frames to detect the raindrop and the fog are set equal each other.

Alternatively, the differential image can be generated not by setting the exposure times for the two frames to the same period, but by correcting the difference of the exposure times using image processing. More specifically, assuming that the exposure time of the frame when the light source 210 is lighted up is "Ta" and the exposure time of the frame when the light source 210 is switched off is "Tb", a difference Yr is obtained by calculating a value obtained by dividing luminance Ya of the light up frame by an exposure time Ta and a value obtained by luminance Yb of the switched off frame by an exposure time Tb as the following formulas 1 through 3. By using the corrected differential image, even though the exposure times between the two frames are different, the effect of the disturbance light can be appropriately eliminated without being affected by the difference of the exposure times.

$$Ya = Ya/Ta \tag{1}$$

$$Yb = Yb/Tb \tag{2}$$

$$Yr = Ya^{20} Yb \tag{3}$$

Yet alternatively, light irradiation intensity of the light source 210 can be controlled depending on the exposure time, without setting the exposure times not to be equal. In this method, the light irradiation intensity of the light source 210 is set at a lower value for the frame having longer exposure time. With this setting, without being affected by the difference of the exposure times, the effect of the disturbance light can be appropriately eliminated using the differential image between the two frames having different exposure times. Furthermore, although the correction based on the image processing has a problem that a processing load is great, in the present method, the correction based on the image processing becomes unnecessary and this problem is not generated.

In general, the LED 211 used as a luminescent material of the light source 210 changes the emission amount depending on change in temperature. As the temperature is increased, the emission output of the light source 210 is decreased. In addition, the amount of light of the LED 211 is decreased due to time deterioration.

When the output of the light source 210 is changed as described above, change in the luminance is recognized in spite of the absence of the raindrop and the fog, and it becomes easy to generate the error detection of the raindrop and the fog. In order to suppress the effect caused by the change in the emission output of the LED 211, in the present embodiment, whether to change the emission output of the LED 211 is arbitrarily determined. When the change in the emission output of the LED 211 is detected, the emission output of the light source 210 is controlled to be increased.

Whether the emission output of the LED 211 is changed is determined as follows. In the present embodiment, since the total reflection light L3 from the outer surface of the windshield 105 is captured as the two-dimensional image in the central region 232A of the foreign substance detecting image region 232, when the emission output of the LED 211 is changed, the luminance in the central region 232A is wholly decreased. In addition, when the outer surface of the windshield 105 is wet with the raindrops, the luminance in the central region 232A is wholly decreased. Therefore it is necessary to distinguish therebetween. In order to distinguish the decreases caused by the deterioration of the LED 211 and by the raindrops, when the luminance in the central region 232A is wholly decreased, the wiper 107 is operated, and then the luminance in the central region 232A is still decreased, the fact that the emission output of the LED 211 is changed is determined.

Figure 25:
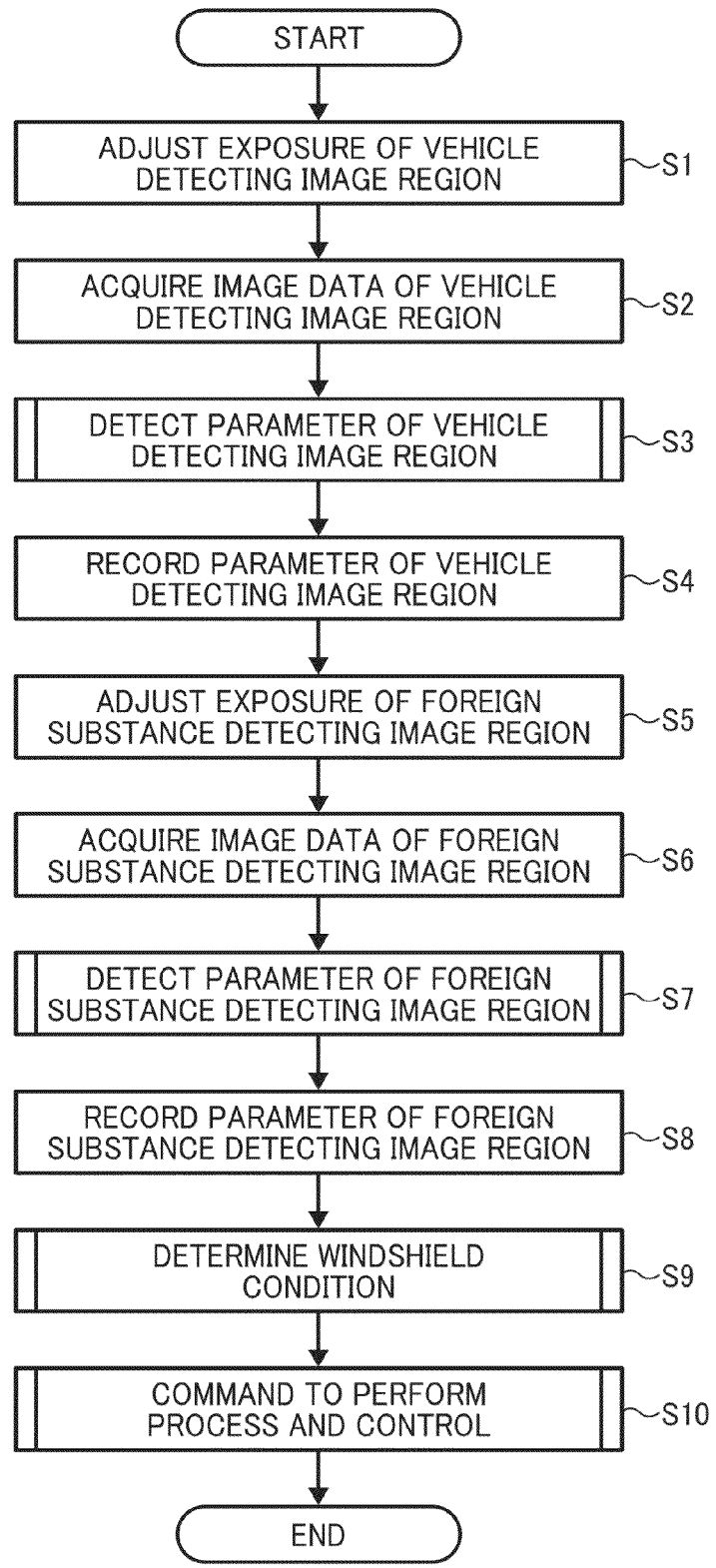
FIG. 25 is a flow chart illustrating a windshield condition detection process executed by an image analyzer shown in FIG. 1.

Next, a windshield condition detection process according to the present disclosure is described below. FIG. 25 is a flow chart illustrating a windshield condition detection process executed by the image analyzer 102. The amount of received light of the foreign substance detection filter 205B that includes spectral filter layer 251 is less than that of the vehicle detection filter 205A that does not contain the spectral filter layer 205B. Therefore, the great difference is generated between the amount of light transmitted through the foreign substance detection filter 205B and the amount of light transmitted through the vehicle detection filter 205A. In addition, there is a great difference between the capturing condition (exposure amount) suitable for the vehicle detecting image region 231 corresponding to the vehicle detecting filter 205A and the capturing condition suitable for foreign substance detecting image region 232 corresponding to the foreign substance detection filter 205B. Therefore, different amounts of exposure are used for capturing the vehicle detecting image region 231 and for capturing foreign substance detecting image region 232.

In the process of adjusting the exposure amount, for detecting other vehicles with respect to the vehicle 100, the exposure amount is automatically adjusted based on the output of the image sensor 206 corresponding to the vehicle detecting image region 231 at step S1, and for detecting the foreign substances, the exposure amount is adjusted to a predetermined fixed value at step S5. When the exposure amount is changed, for example, the exposure time is changed. More specifically, the image analyzer 102 controls a time period during which the image sensor 206 converts the amount of receiving light into an electrical signal, thereby changing the exposure time.

The vehicle detecting image region 231 is acquired by capturing the vicinity of the vehicle. The luminance around the vehicle changes from 1 lux or less in the night time to several ten thousands lux in the daytime, and the amount of receiving light greatly changes depending on the capturing scenes. Accordingly, it is necessary to adjust the exposure time appropriately depending on the capturing scene. It is desirable for the vehicle detecting image region 231 to adjust the exposure amount by using known automatic exposure control.

By contrast, the foreign substance detecting image region 232 is captured by receiving a predetermined intense of the light emitted from the light source 210 through the optical filter 205 having a known transmission, and the change in the amount of receiving light is low. Accordingly, the exposure amount is not automatically adjusted in the foreign substance detecting image region 232, and the image can be captured at the fixed exposure time. By using the fixed exposure time, the control time of the exposure amount can be shortened and control of the exposure amount can become simple.

In FIG. 25, after the expose amount for the vehicle detecting image region 231 is adjusted at step S1, the image analyzer 102 acquires the image data for the vehicle detecting image region 231. In the present embodiment, the image data for the vehicle detecting image region 231 is used not only for detecting vehicle, lane makers, and road signs, but also for controlling the wiper 107 and the defroster 110, which is described in detail below. Accordingly, the image analyzer 102 that acquires the image data of the vehicle detecting image area, detects a parameter for controlling the wiper 107 and the defroster 110 at step S3, and stores the detected parameters in a certain storage area at step S4.

Figure 26:
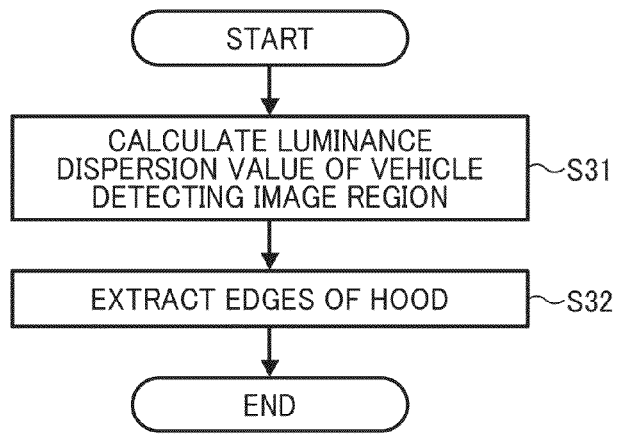
FIG. 26 is flow chart illustrating a process to detect parameters for controlling a wiper and a defroster based on the image data, of the vehicle detecting image region.

FIG. 26 is flow chart illustrating a process to detect the parameters for controlling, the wiper 107 and the defroster 110 based on the image data, of the vehicle detecting image region 231. In the present embodiment, the luminance dispersion in the vehicle detecting image region 231 is used as the parameters detected for controlling the wiper 107 and the defroster 110 at step S31. In addition, in the present embodiment, as for this parameter, the capturing area is set so that an edge area between the hood 100a of the vehicle 100 and the background ahead can be detected, and the edge extract result of the hood 100a is used at step S32.

Figure 27:
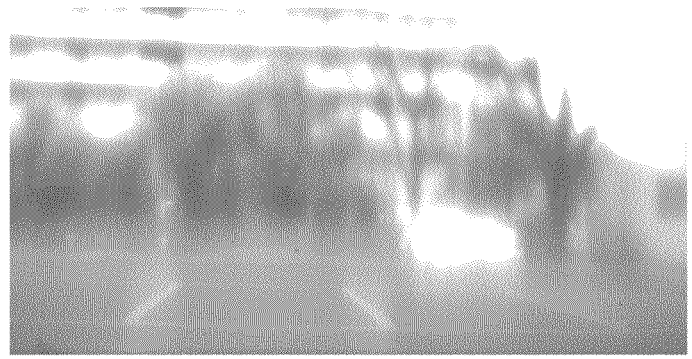
FIG. 27 is an illustration of the captured image showing the state in which the windshield is fogged.
Figure 28:
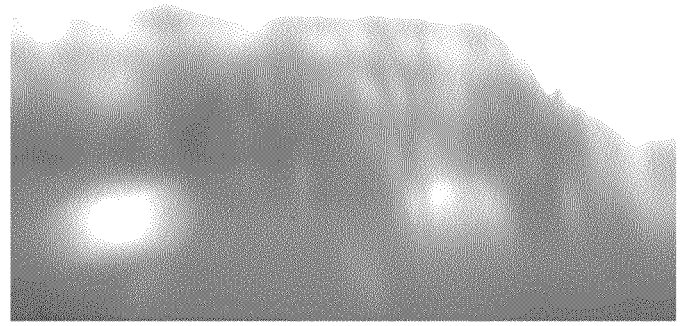
FIG. 28 is an illustration of the captured image showing the state in which the windshield is frozen.

FIG. 27 is an illustration of the captured image showing the state in which the inner surface of the windshield 105 is fogged. FIG. 28 is an illustration of the captured image showing the state in which the outer surface of the windshield 105 freezes up.

When the inner surface of the windshield 105 is fogged as illustrated in FIG. 27, or when the external surface of the windshield 105 freezes up as illustrated in FIG. 28, the image of the vehicle detecting image region 231 has smaller luminance dispersion. Accordingly, the luminance dispersion in the vehicle detecting image region 231 is useful for detecting the condition whether or not the fog or the ice forms on the windshield 105. When the windshield 105 fogs up or freezes up, extracting the edge areas of the hood 100a becomes difficult. Accordingly, the information of whether the edge areas of the hood 101a can be extracted or not is useful for detecting that the fog or the ice forms on the windshield 105.

Referring back to FIG. 25, as for the foreign substance detecting image region 232, the exposure (exposure time) is adjusted based on the power of the light source 210 and the spectral characteristics of the spectral filter 251 in the optical filter 250 at step S5. Subsequently, the image analyzer 102 acquires the image data of the foreign substance detecting image region 232 at step S6. Then, the image analyzer 102 detects a parameter for controlling the wiper 107 and defroster 110 from the image data of the foreign substance detecting image region 232 at step S7, and then stores the parameter in the certain storage area at step S8.

Figure 29:
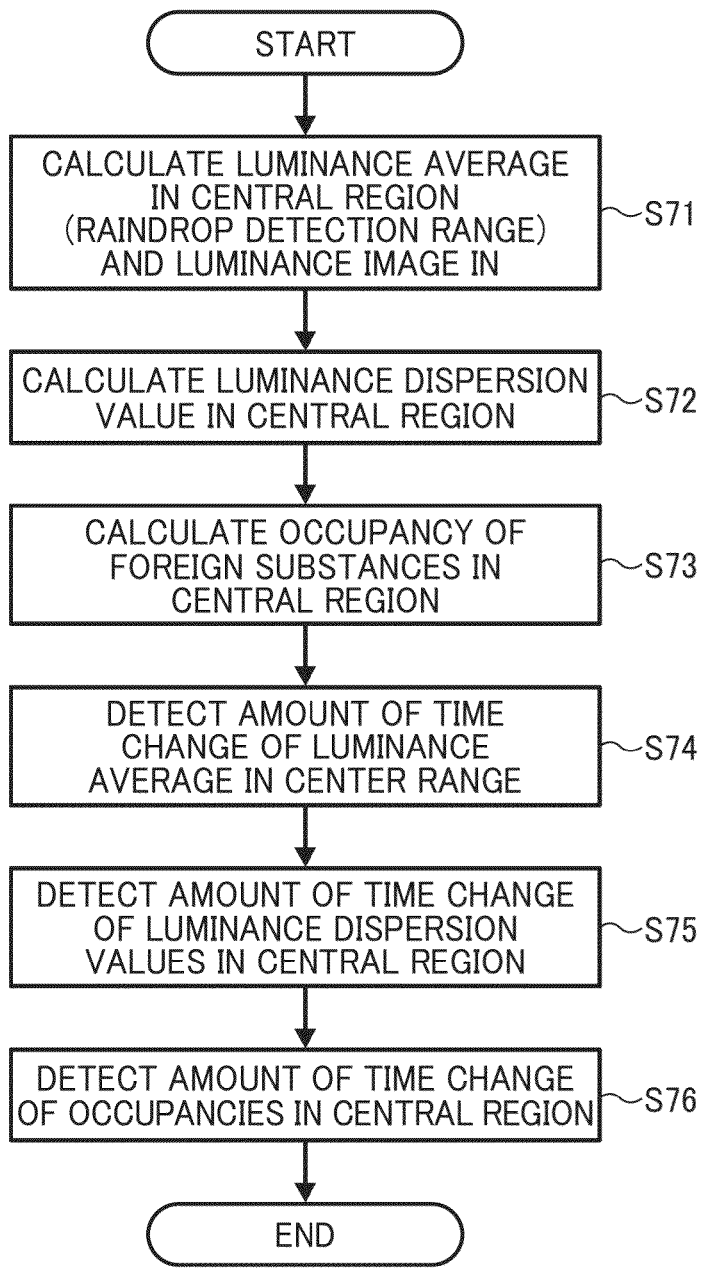
FIG. 29 is a flow chart illustrating the process to detect the parameters for controlling the wiper and the defroster from the image data of the foreign substance detecting image region.

FIG. 29 is a flow chart illustrating the process to detect parameters for controlling the wiper 107 and the defroster 110 based on the image data of the foreign substance detecting image region 232. In the present embodiment, as the parameter detected for controlling the wiper 107 and the defroster 110, the image analyzer 102 calculates a luminance average in the central region 232A (raindrop detecting range, outer surface light receiving region) corresponding to the first light receiving member 206 (receives light reflected from the outer surface of the windshield 105) and as luminance average in the both end regions 232B (fog detecting range, inner surface light receiving region) corresponding to the second light receiving member 206 (receives light reflected from the inner surface of the windshield 105) in the foreign substance detecting image region 232 at step S71. In this example, when the raindrop, the fogs, and the ice are present on the outer surface of the windshield 105, the luminance average in the center area 232A of the foreign substance detecting image region 232 is decreased. Accordingly, whether or not the substance is present on the outer surface of the windshield 105 can be detected based on the luminance average of the central region 232A. In addition, when the fog is present on the inner surface of the windshield 105, the luminance average of the both end regions 232B of the foreign substance detecting image region 232 is increased. Accordingly, whether or not the fog forms on the inner surface of the windshield 105 can be detected based on the luminance average of the both end regions 232B.

Further, in the process shown in FIG. 29, as for the parameter detected for controlling the wiper 107 and the defroster 107, luminance dispersion is calculated in the central region (raindrop detecting region) 232A of the foreign substance detecting image region 232 at step S72. When it drizzles (when the raindrops have small sizes), since the total area size of the raindrops showing in the central region 232A is small, the luminance dispersion does not much vary, compared to the condition in which substance is not present on the windshield 105. However, when the amount of the foreign substances of the raindrops having relatively large size present on the windshield 105 is increased, the luminance dispersion is decreased. This is why the fuzzy images of raindrops are superimposed respectively. Similarly, when the windshield 105 fogs up and freeze up on the outer surface of the windshield 105, the luminance dispersion becomes small. With this process, the image analyzer 102 can detect whether the sizes of substances present on the windshield 105 are nearly drizzles or not based on the luminance dispersion of the central region 232A.

In addition, as the parameter detected for controlling the wiper 107 and the defroster 110, the occupancy of the foreign substances (area) 203 in the central region 232A of the foreign substance detection image section 232 is calculated at step S73. The occupancy of the foreign substances 203 means the ratio of the number of pixels (area of foreign substance image 203) where the luminance average exceeds the defined value in the central region 232A relative to the total number of pixels (total area) of the center section 232A. Since the occupancy of the foreign substances 203 is generally large in the foggy area and the frozen area, whether the foreign substances are not the drizzle but the fogging or freezing, can be detected based on the occupancy of the foreign substances 203 of the central region 232A.

In addition, as for the parameter detected for controlling the wiper 107 and the defroster 110, time changes in the above-described luminance average, luminance dispersion, and occupancy of the foreign substances 203 in the central region (raindrop detection range) 232A are detected. The time change means the changing amount based on the present captured image data of the central region 232A and previously captured image data of the central region 232A. Although the fogs and the ice are not rapidly increased in a short time, splash (spray of water when another vehicle splashes water on the vehicle 100) present on the windshield 105 is rapidly increased in a shot time. Accordingly, whether the substance present on the windshield 105 is caused by splash or not can be detected based on the time change of the luminance average, the luminance dispersion, and the occupancy of the foreign substances 203 in the central region 232A.

Figure 30:
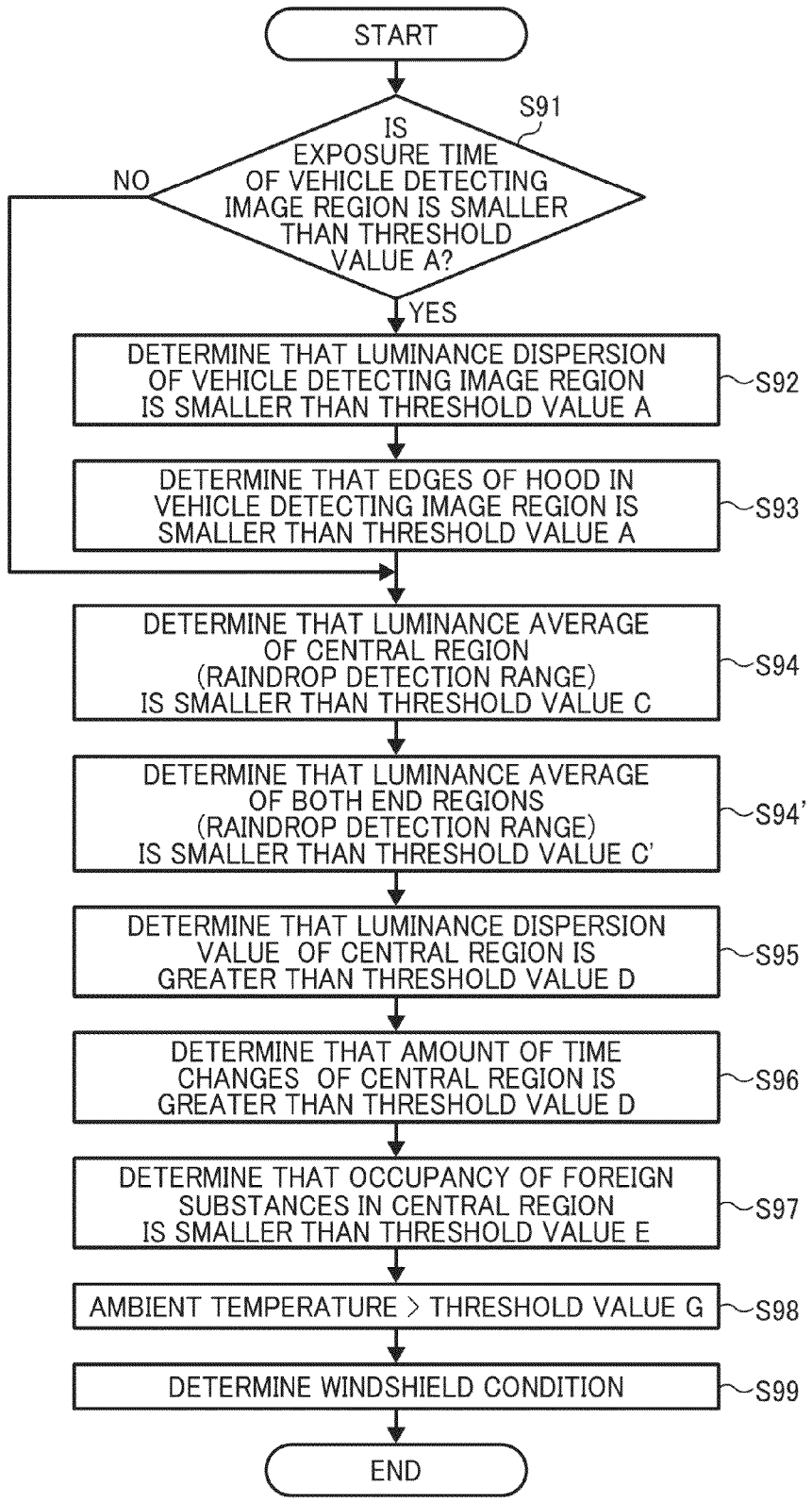
FIG. 30 is a flow chart illustrating a windshield condition determination process.

In FIG. 25, after the parameter for controlling the wiper 107 and defroster 110 is stored, the condition of the windshield 105 is determined at step S9. FIG. 30 is a flow chart illustrating a condition determination process for the windshield 105. FIG. 31A is a table illustrating daytime determination criteria of the windshield condition determination process, and FIG. 31B is table illustrating nighttime determination criteria thereof. In the condition determination process of the windshield 105, initially, the image analyzer 102 determines whether the exposure time decided by the automatic exposure adjustment for the vehicle detecting, image region 231 is shorter than a threshold value (e.g., 40 ms). When the exposure time is set at a long time such as a time longer than is threshold value A, it can be seen that the amount of light in the vehicle detecting image region 231 is few and the image 23 is captured at night. Thus, the captured image can be distinguished between day and night by detecting whether or not the exposure time is set shorter than the threshold value A.

When the image 23 is captured at night, the determination accuracy of the windshield 105 calculated based on the parameters (luminance dispersion, edge extraction of the hood) from the image data of the vehicle detecting image region 231 is low. In the embodiment, when the condition is determined as at night, the parameters (luminance dispersion, edge extraction of the hood) from the image data of the vehicle detecting image region 231 are not used, the condition of the windshield 105 is determined using only the parameter from the foreign substance detecting image region 232, with reference to FIG. 31B.

When it is determined that the image 23 is captured in daytime at step S91, subsequently, the image analyzer 102 determines that the luminance dispersion of the vehicle detecting image region 231 is greater than a threshold value B at step S92. The determination result is stored in the predetermined storage device. A table depending on the exposure time based on experiment is prepared, and the threshold value B is determined in accordance with the respective exposure times.

By contrast, when the image is captured in the daytime is detected at step S91, the image analyzer 102 determines whether the edge areas of the hood 101a of the vehicle detecting image region 231 can be extracted at step S93, with reference to FIG. 31A. The determination result is stored in the predetermined storage memory. In the process of extracting edges of the hood 101a, for the vehicle detecting image region (capturing image receiving region) 231 containing the hood 101a and the background, from the luminance change of the adjacent pixels in a vertical direction, a differential image of the horizontal edge components is generated. The differential image of the horizontal edge components is compared by pattern matching with the differential image being previously stored. When the respective pattern matching errors detected based on the result of the respective pattern comparison is smaller than the threshold value, it is determined that the edge area of the hood can be detected. When the edge area can be detected, absence of any fogging, freezing, and splash on the windshield 105 can be determined.

Then, the image analyzer 102 determines that the various types of parameters acquired from the foreign substance detecting image area. Initially, whether the luminance average in the central region 232A of the foreign substance detecting image region 232 is smaller than a threshold value C is determined at step S94. The determination result is stored in the predetermined storage memory. As described above, when the raindrop is present on the windshield 105, the luminance average of the central region 232A is decreased. For example, when the luminance of the foreign substance detecting image region 232 has 1024 gradation levels, whether the luminance average smaller than to threshold value C (900 gradations obtained by removing noise elements) is determined.

At step S94', whether the luminance average of both end regions 232B of the foreign substance detecting image region 232 is greater than a threshold value C' at step S94' is determined. The determination result is stored in the predetermine storage memory. As described above, when the fog is present on the inner surface of the windshield 105, the luminance average in the both end regions 232B is increased.

At step S95, whether the luminance dispersion of the central region 232A of the foreign substance detecting image region 232 is greater than a threshold value D is determined. The determination result is stored in the predetermined storage device. For example, if the luminance of the foreign substance detecting image region 232 has 1024 gradations, and when the luminance dispersion is greater than 50 (threshold value D), it can be determined that the fog is not present and ice does not form on the windshield 105.

At step S96, whether the time change in the luminance average in the central region 232A of the foreign substance detecting image region 232 is smaller than a threshold value E is determined. The determination result is stored in the predetermined storage memory. For example, when the amount of time change is equal to or greater than the threshold value E (e.g., 200), for example, and when the luminance average of the present captured foreign substance detecting image region 232 is smaller than 700 although the luminance average of the previously captured foreign substance detecting image region 232 is equal to or greater than 900, the occurrence of splash can be determined.

At step S97, whether the occupancy of the foreign substances 203 in the central region 232A of the foreign substance detecting image region 232 is smaller than a threshold value F is determined. The determination result is stored in a predetermined storage area. For example, in a state in which the light source 210 uniformly emits light, and when the area where the luminance average is smaller than 900 (threshold value) falls below one fifth (threshold value F), it is determined that the foreign substances is the drizzle. When the area where the luminance average is smaller than 900 (threshold value) falls below one fifth (threshold value F) is equal to or greater than one fifth, the image analyzer 102 determines that another types of substances are present.

At step S98, as for the parameter detected for controlling the wiper 107 and the defroster 110, the detection result of ambition sensor 111 is used. The image analyzer 102 determines whether the ambient temperature detected by the ambient sensor 111 is greater than the threshold value G. The determination result is stored in the predetermined storage memory. For example, when the ambient temperature is equal to or lower than 0 degree, (threshold value G), it can be determined that it snows or windshield is iced.

After the determination result about respective parameters are acquired, the image analyzer 102 determines the condition of the windshield 105 based on consistency of the determination result of the respective parameters with the tables shown in FIGS. 31A and 31B. In the condition determination process, the image analyzer 102 weights the determination results of the respective parameters. For example, a weighting coefficient of 1 is assigned to the parameters based on the foreign substance detecting image region 232 and a parameter of ambient temperature, and a weighting coefficient of 5 is assigned to the parameter of the vehicle detecting image region 231. Then, as for the determination result of the respective parameters, the area where difference is generated from the shine state is weighted as 1, and the area where there is no difference from the shine state is weighted as 0. Subsequently, threshold value determination is perforated for the sum acquired by multiplying the determination results of the respective parameters by multiplying the weighting coefficients. Accordingly, even when there is no condition in which the determination results of the respective parameters perfectly matches the tables shown in FIGS. 31A and 31B, which enables the condition determination of the windshield 105.

In addition, for each of determination targets, the weighting of the respective parameters may be adjusted depending on the reliability of the determination of the determination targets. For example, when the foggy condition is detected, the determination result (S94') of the luminance average of the both end regions 232B in the foreign substance detecting image region 232 may be weighted relatively heavy. Alternatively, when the difference is generated from the state of normal for the parameter of the foreign substance detecting, image region 232, after operating the wiper once, the condition determination of the respective parameters can be confirmed.

Referring back to FIG. 25, after the determination result of the condition of the windshield 105 is output, the image analyzer 102 commands to perform the processes and control (wiper control and defroster control) depending on the condition determination result at step S10.

The command process is performed depending on the table shown in FIG. 32. In the process of wiper control, the wiper speed has three stages (high, medium, and slow). In the process of defroster contra whether or not the hot air of maxim airflow is blown to the inner surface of the windshield 105 is controlled.

In the above-description, the reflection-polarization prism 220 is used as the optical device containing the reflection face 221 and the reflection member (light-guiding member) 226 that reflects the light emitted from the light source 210; alternatively, the optical device may be formed by a mirror member having a reflection surface.

As described above, the foreign substance detection system 300, provided close to a planner light-transmissive plane member 105, detects substances present on the planner light-transmissive plane member 105. The foreign substance detection system 300 includes a light emitting member 210, an optical device 220, a light-guiding member 226, a first light receiving member 206, a second light receiving member 206, and a foreign substance detection processor 102.

The light emitting member 210, positioned on an inner surface side of the planner light-transmissive member 105, emits light toward the inner surface of the planner light-transmissive member 105. The optical device 220 has an input surface 223 and a transparent face 222. A part of the light emitted from the light emitting element 210 enters the optical device 220 through the input surface 223. The transparent face 222, provided in close contact with the inner surface of the planner light-transmissive member 105, transmits a light reflected from an outer non-substance detected area where a substance is not present on an outer surface of the planner light-transmissive member 105. The light-guiding member 226 guides another part of the light that does not pass through to the input surface 223 of the optical device 220 toward the planner light-transmissive member 105. The guided light is to be reflected from an inner substance detected area where a substance is present on the inner surface of the planner light-transmissive member 105. The first light receiving member 206 receives the light reflected from the outer non-substance detected area where the substance is not present on the outer surface of the planer light-transmissive member 105 and transmitted through the transparent face 222 of the optical device 220. The second light receiving member 206 receives the light guided by the light-guiding member 226 and reflected from the inner substance detected area where the substance is present on to the inner surface of the planner light-transmissive member 105. The foreign substance detection processor 102 detects the substance present on the outer surface of the light-transmissive plane member 105 based on the receiving result of the first light receiving member 206, and detects the substance present on the inner surface of the planner light-transmissive member 105 based on the receiving result of the second light receiving member 206.

With this configuration, the transparent face 222 of the optical device 220 is provided in closely contact with the inner surface of the planner member 105. Compared to a configuration in which a clearance is formed between the transparent face 222 of the optical device 220 between the inner surface of the planner member 105, in the present configuration, the transparent face 222 can make an incident angle to the inner surface of the planner member 105 so that the light transmitted through the transparent face 222 of the optical device 220 can be reflected from the outer non substance detected area of the planner member 105 at a high reflection rate, and the light transmitted through the transparent face 222 of the optical device 220 can be reflected from the outer non substance detected area of the planner member 105 at a low reflection rate. Accordingly, a difference between the amount of lights reflected from the outer substance detected area and the outer non-substance detected area, received in the first light receiving member 206 can be set greater, such that the detection accuracy of the outer foreign substance can be improved.

However, since the clearance is not formed between the transparent face 222 of the optical device 220 between the inner surface of the planner member 105 and the transparent face 222 of the optical device 220, the substance present on the inner surface of the planner member 105 cannot be detected by the optical device 222. In order to solve this problem, the light-guiding member (reflection mirror 226) guides another part of light that does not pass through to the input surface 223 of the optical device 220 toward the planner member 105, and the guided light is to be reflected from an inner substance detected area where a substance is present on the inner surface of the planner light-transmissive member 105. Then, the second light receiving member 206 receives the light guided by the light-guiding member 226 and reflected from the inner substance detected area where the substance is present on to the inner surface of the planner light-transmissive member 105.

With this configuration, while the detection accuracy of the outer foreign substance can be improved by providing the transparent face 222 of the optical device 220 in contact with the inner surface of the planner member 105, the inner foreign substance can be detected.

The foreign substance detection system 300 further includes an imaging device 101, having a light receiving face (image sensor 206), to capture an image of the substance present on the outer surface of the planner light-transmissive member 105. The light receiving face 206 has an outer surface light receiving region 232A constituting the first light receiving member 206 showing the substances present on the outer surface of the planner light-transmissive member 105. The light receiving face 206 has an inner surface light receiving region 232B constituting the second light receiving member 206 different from the outer surface light receiving region 232A.

With this configuration, the first light receiving member 232A showing the substances present on the outer surface of the planner light-transmissive member 105, and the second light receiving member 232B showing the substances present on the outer surface of the planner light-transmissive member 105 are configured as a single image capturing unit 101, such that the members of the device can be eliminated.

In the foreign substance detection system 300, the inner surface light receiving region 232B is positioned in an area so as not to receive the light specular reflected from the outer non-substance detected area where the substance is not present on the outer surface of the planner light-transmissive member 105.

With this configuration, the inner foreign substance can be detected in a state in which the outer foreign substance can be detected with low adversely influence of the light. In addition, while the first light receiving region 232A and the second light receiving region 232B are configured as a single capturing unit 200, degradation in accuracy of the foreign substances can be suppressed.

In the foreign substance detection system 300, the light receiving face 206 of the image capturing device 101 further has a captured image receiving region 231 to receive a transmissive light from a predetermined capturing image area (upper area) showing an area ahead of the foreign substance detection system 300.

With this configuration, using the image capturing unit 101 that captures the area ahead of the planner member 105, the substances present on the inner surface and the outer surface of the planner member 105 can be detected.

In the foreign substance detection system 300, the light-guiding member 226 includes a light reflection member 226 to reflect the light that is emitted from the light emitting element 210 and does not enter the inside of the optical device 220 through the input surface 223.

With this continuation, a flexibility of the layout in the light guide member 226 is improved.

In the foreign substance detection system 300, the optical device 220 includes a prism 220, and the light guiding member 226 has one outer face of the prism 220 to reflect the light that is emitted from the light emitting element 210 and is not input to the input surface 223 of the optical device 220.

With this continuation, the optical device (220, 222, 223) and the light-guiding member 226 are integrally configured as a single unit, such that the number of members in the device can be decreased.

In the foreign substance detection system 300, the optical device 220 includes a reflection face 221 to reflect the light that is emitted from the light emitting element 210 and is input to inside of the optical device 220 through the input surface 221.

With this configuration, a flexibility of the layout in the optical device is improved.

In the foreign substance detection system 300, at least one of the first light receiving member 206 and the second light receiving member 206 has a spectral filter 205 to selectively transmit the light of a certain wavelength, emitted from the light emitting element 210.

With this configuration, the adversely influence from the ambient light when the foreign substance is detected can be alleviated, and the detection accuracy of the foreign substance can be improved.

In addition, a moving body controller (102, 103, 106, 108, 109), installed in a moving body 100 that has at least one operational device (104, 107, 110), includes at least one control device (103, 106, 108, 109) and a foreign substance detection system 300). The control device (103, 106, 108, 109) controls operation of the operational device (104, 107, 110) or movement of the moving body 100. The foreign substance detection system 300 positioned close to a window 105, detects substances present on the window 105, operatively connected to the control device (103, 106, 108, 109). The foreign substance detection system 300 includes a light emitting member 210, an optical device 220, as light-guiding member 226, a first light receiving member 206, a second light receiving member 206, and a foreign substance detection processor 102. The light emitting element 210, positioned on an inner surface side of the window 105, emits light to the inner surface of the window 105. The optical device 220 has an input surface 223 and a transparent face 222. A part of light emitted from the light emitting element 210 inputs to the optical device 220 through the input surface 223. The transparent face 222, provided in contact with the inner surface of the planner light-transmissive member 105, transmits a light reflected from an outer non-substance detected area where a substance is not present on an outer surface of the window 105. The light-guiding member 226 guides the remaining light that does not pass through to the input surface 223 of the optical device 220 to reflect the light so that the output light is reflected from an inner substance detected area where a substance is not present on an inner surface of the window 105. The first light receiving member 206 receives the light reflected from the outer non-substance detected area where the substance is not present on the outer surface of the window 105 and transmitted through the transparent face 222 of the optical device 220. The second light receiving member 206 receives the light guided by the light-guiding member 226 and reflected from the inner substance detected area where the substance is present on to the inner surface of the window 105. The foreign substance detection processor 102 detects the substance present on the outer surface of the window 105 based on the receiving result of the first light receiving member 206, detects the substance present on the inner surface of the window 105 based on the receiving result of the second light receiving member 206, and outputs the detection result to the control devices (103, 106, 108, 109).

With this configuration, various target devices can be controlled by using the detection result of the substances present on the outer surface and the inner surface of the window 105.

A moving body 100 includes the window 105 and the above-described moving body controller (102, 103, 106, 108, 109), to control controlled objects in the moving body.

With this configuration, the moving body that can control various target devices can be achieved.

Numerous additional modifications and variations are possible in light of the above teachings. It is therefore to be understood that, within the scope of the appended claims, the disclosure of this patent specification may be practiced otherwise than as specifically described herein.

What is claimed is:

1. A foreign substance detection system, provided close to a planner light-transmissive plane member, to detect substances present on the planner light-transmissive plane member, the foreign substance detection system comprising:
a light emitting member to emit light toward the inner surface of the planner light-transmissive member;
an optical device, having an input surface through which a part of the light emitted from the light emitting element enters the optical device and a transparent face, provided in close contact with the inner surface of the planner light-transmissive member, to transmit a light reflected from an outer non-substance detected area where a substance is not present on an outer surface of the planner light-transmissive member;
a light-guiding member to guide another part of the light that does not pass through the input surface of the optical device toward the planner light-transmissive member, the guided light being to be reflected from an inner substance detected area where a substance is present on the inner surface of the planner light-transmissive member;
a first light receiving member to receive the light reflected from the outer non-substance detected area where the substance is not present on the outer surface of the planner light-transmissive member and transmitted through the transparent face of the optical device;
a second light receiving member to receive the light guided by the light-guiding member and reflected from the inner substance detected area where the substance is present on the inner surface of the planner light-transmissive member; and
a foreign substance detection processor to detect the substance present on the outer surface of the light-transmissive plane member based on the receiving result of the first light receiving member, and detect the substance present on the inner surface of the planner light-transmissive member based on the receiving result of the second light receiving member.

2. The foreign substance detection system according to claim 1, further comprising:
an imaging device, having a light receiving face, to capture an image of the substance present on the outer surface of the planner light-transmissive member,
wherein the light receiving face comprises an outer surface light receiving region constituting the first light receiving member showing the substances present on the outer surface of the planner light-transmissive member, and
the light receiving face comprises an inner surface light receiving region constituting the second light receiving member different from the outer surface light receiving region.

3. The foreign substance detection system according to claim 2, wherein the inner surface light receiving region is positioned in an area so as not to receive the light specularly reflected from the outer non-substance detected area where the substance is not present on the outer surface of the planner light-transmissive member.

4. The foreign substance detection system according to claim 2, wherein the light receiving face of the image capturing device further comprises a captured image receiving region to receive a transmissive light from a predetermined capturing image area showing an area ahead of the foreign substance detection system.

5. The foreign substance detection system according to claim 1, wherein the light-guiding member comprises a light reflection member to reflect the light that is emitted from the light emitting element and does not enter the inside of the optical device through the input surface.

6. The foreign substance detection system according to claim 5, wherein the optical device comprises a prism, and the light guiding member comprises one outer face of the prism to reflect the light that is emitted from the light emitting element and is not input to the input surface of the optical device.

7. The foreign substance detection system according to claim 1, wherein the optical device comprises a reflection face to reflect the light that is emitted from the light emitting element and is input to inside of the optical device through the input surface.

8. The foreign substance detection system according to claim 1, wherein at least one of the first light receiving member and the second light receiving member comprises a spectral filter to selectively transmit the light of a certain wavelength, emitted from the light emitting element.

9. A moving body controller, installed in a moving body that has at least one operational device, comprising:
at least one control device to control operation of the operational device or movement of the moving body;
a foreign substance detection system positioned close to a window, to detect substances present on the window, operatively connected to the control device,
the foreign substance detection system comprising:
a light emitting element, to emit light toward the inner surface of the window;
an optical device, having an input surface through which a part of light emitted from the light emitting element enters the optical device and a transparent face, provided in close contact with the inner surface of the window, to transmit a light reflected from an outer rim-substance detected area where a substance is not present on an outer surface of the window;

a light-guiding member to guide another part of the light that does not pass through the input surface of the optical device toward the window, the guided light being to be reflected from an inner substance detected area where a substance is present on the inner surface of the window;

a first light receiving member to receive the light reflected from the outer non-substance detected area where the substance is not present on the outer surface of the window and transmitted through the transparent face of the optical device;

a second light receiving member to receive the light guided by the light-guiding member and reflected from the inner substance detected area where the substance is present on the inner surface of the window; and an foreign substance detection processor to detect the substance present on the outer surface of the window based on the receiving result of the first light receiving member, and detect the substance present on the inner surface of the window based on the receiving result of the second light receiving member, and output the detection result to the control device.

10. A moving body comprising:
a window;
at least one operational device;
a moving body controller comprising:
  at least one control device to control operation of the operational device or movement of the moving body;
  a foreign substance detection system positioned close to a window, to detect substances present on the window, operatively connected to the control device,
the foreign substance detection system comprising:
a light emitting element, to emit light toward the inner surface of the window;
an optical device, having an input surface through which a part of the light emitted from the light emitting element enters the optical device and a transparent face, provided in close contact with the inner surface of the window, to transmit a light reflected from an outer non-substance detected area where a substance is not present on an outer surface of the window;
a light-guiding member to guide another part of the light that does not pass through the input surface of the optical device toward the window, the guided light being to be reflected from an inner substance detected area where a substance is present on the inner surface of the window;
a first light receiving member to receive the light reflected from the outer non-substance detected area where the substance is not present on the outer surface of the window and transmitted through the transparent face of the optical device;
a second light receiving member to receive, the light guided by the light-guiding member and reflected from the inner substance detected area where the substance is present on to the inner surface of the window; and
an foreign substance detection processor to detect the substance present on the outer surface of the window based on the receiving result of the first light receiving member, and detect the substance present on the inner surface of the window based on the receiving result of the second light receiving member, and output the detection result to the control device.

\* \* \* \* \*